United States Patent [19]
Schofield

[11] Patent Number: 6,019,006
[45] Date of Patent: Feb. 1, 2000

[54] CENTRIFUGES AND ASSOCIATED APPARATUS AND METHOD

[75] Inventor: Andrew Noel Schofield, Cambridge, United Kingdom

[73] Assignee: Andrew N. Schofield & Associates Limited, Cambridge, United Kingdom

[21] Appl. No.: 08/846,158

[22] Filed: Apr. 25, 1997

Related U.S. Application Data

[62] Division of application No. 08/162,124, filed as application No. PCT/GB92/01046, Jun. 11, 1992, Pat. No. 5,634,876.

[30] Foreign Application Priority Data

Jun. 11, 1991 [GB] United Kingdom .................... 9112585
Jan. 11, 1992 [GB] United Kingdom .................... 9200552

[51] Int. Cl.[7] ...................................................... B04B 9/12
[52] U.S. Cl. ............................................................ 73/865.6
[58] Field of Search ................................. 73/865.3, 865.6, 73/866.4, 38; 494/10

[56] References Cited

U.S. PATENT DOCUMENTS

| | | | |
|---|---|---|---|
| 4,375,272 | 3/1983 | Sutton, III | ................................. 494/10 |
| 4,385,524 | 5/1983 | Cappel . | |
| 4,919,646 | 4/1990 | Perdriat . | |
| 5,133,208 | 7/1992 | Ricci | ......................................... 494/10 |

*Primary Examiner*—Robert Raevis
*Attorney, Agent, or Firm*—William D. Hall

[57] ABSTRACT

A scale modelling centrifuge has a relatively massive rotary circular base wall, which may form part of a drum, possibly with a detachable peripheral wall either carrying an annular sample-reciving trough or constituted by such trough, or which may have mounted therearound a plurality of sample-receiving containers.

14 Claims, 19 Drawing Sheets

CENTRIFUGES AND ASSOCIATED APPARATUS AND METHOD

CROSS-REFERENCES TO RELATED APPLICATIONS

This Application is a Division of my prior U.S. patent application Ser. No. 08/162,124 filed Dec. 13, 1993 now U.S. Pat. No. 5,634,876. That prior Application was the National Phase of International Patent Application PCT/GB92/01046 filed Jun. 11, 1992.

TECHNICAL FIELD

This invention relates to centrifuges and centrifuging methods, particularly but not exclusively for scale modelling, especially in the geotechnical field, and to associated apparatus and methods.

DISCLOSURE OF INVENTION

According to a first aspect of the present invention, there is provided a centrifuge comprising a substantially horizontal rotary wall having an annular outer periphery and rotatable about its own axis, bearing means mounting said wall for rotation about said axis, which is substantially vertical, a work support located centrally of said wall, rotary receiving means supported by said wall, located in the region of said outer periphery and accessible from said work support, and stationary means relative to which said wall and said receiving means are rotatable.

The support can be used to support experimental testpieces, tools, or an operator. It may be fixed, or be rotatable with the rotary wall, or be rotatable relative to the rotary wall. The support may take the form of a vertical shaft (i.e. a column) or a platform, for example a turntable.

According to a second aspect of the present invention, there is provided a centrifuge, comprising a rotary wall having an annular outer periphery and rotatable about its own axis, bearing means mounting said wall for rotation about said axis, a work support so mounted centrally of said wall as to be retractable axially of said wall and as to be able to remain stationary while said wall rotates, rotary receiving means supported by said wall, located in the region of said outer periphery and accessible from said work support, and stationary means relative to which said wall and said receiving means are rotatable.

According to a third aspect of the present invention, there is provided a centrifuging method comprising providing a centrifuge including a rotary wall having an annular outer periphery and rotatable about its own axis and rotary receiving means supported by said wall and located in the region of said outer periphery, rotating said wall and said receiving means about said axis and, while said wall and said receiving means rotate, axially retracting relative to said wall and said receiving means a work support mounted centrally of said wall.

This arrangement has the advantage of allowing the work support to be retracted into a relatively accessible position even during centrifuging.

According to a fourth aspect of the present invention, there is provided a centrifuge comprising a rotary wall having an annular outer periphery and rotatable about its own axis, and rotary receiving means releasably attached to a face of said wall in the region of said periphery for containing a scale modelling sample.

An advantage of having the receiving means detachable from the rotary wall is that the scale modelling sample can be prepared in its receiving means in a convenient manner at a suitable remote location, for example in a consolidometer, and then the sample and its receiving means attached to the rotary wall. In this way, the centrifuge can be used much more efficiently than if the sample were prepared in the centrifuge itself.

The receiving means may be an annular trough facing inwards, in which case the rotary wall and the trough form a drum, or the receiving means may be a plurality of containers distributed around the outer peripheral region of the wall, in which case the containers may be radially outwardly encircled by an annular shroud, again giving the appearance of a drum, to reduce wind drag.

According to a fifth aspect of the present invention, there is provided a centrifuge comprising a member rotatable about an axis, scale model means carried by said member at a spacing from said axis, and tilting means arranged to tilt said member so as to tilt said axis between a substantially vertical first condition and a second condition at a substantial angle to the vertical.

According to a sixth aspect of the present invention, there is provided a centrifuging method comprising rotating a centrifuge member while its axis of rotation is at a substantial angle to the vertical, and then tilting said member to tilt said axis to a substantially vertical condition.

The member, which may be an arm or a drum, is advantageously so disposed that the substantial angle is a right-angle, i.e. the longitudinal axis is substantially horizontal.

This arrangement has the advantage that static balancing of one or more scale model(s) (and one or more counterweights) on the member is simplified because the member tends to turn under gravity unless in static balance. The rotation of the member to subject the scale model(s) to high centrifugal force can be performed either with the axis still at that substantial angle to the vertical or after tilting of the axis into a vertical condition.

According to a seventh aspect of the present invention, there is provided a centrifuge comprising a substantially horizontal rotary wall having an annular outer periphery and rotatable about its own axis, rotary receiving means supported by said wall and located in the region of said outer periphery, and access-permitting means in said wall permitting access from below by an operator.

Advantageously, the operator can introduce from below at least the upper part of his body, preferably such that he can stand upright whilst carrying out work in the region of the receiving means. For that purpose, at least one closable manhole is provided in the rotary wall. Materials can also be introduced through such manhole(s). In order that the operator may be able to reach the manhole(s), the rotary wall is spaced upwards from the floor, preferably at about the level of the operator's hips.

A drum formed by the rotary wall and the receiving means may alternatively or additionally be provided with an access at the top thereof, again to allow an operator or materials to be introduced into the interior of the drum.

According to an eighth aspect of the present invention, there is provided a centrifuge comprising a rotary wall having an annular outer periphery and rotatable about its own axis, rotary receiving means supported by said wall and located in the region of said outer periphery, scale model means received by said receiving means, and stationary means relative to which said wall is rotatable.

According to a ninth aspect of the present invention, there is provided a centrifuging method, comprising providing a centrifuge including a rotary wall having an annular outer periphery and rotatable about its own axis and rotary receiving means supported by said wall and located in the region of said outer periphery, introducing scale model means into said receiving means, and rotating said wall and said receiving means about said axis to subject said scale model means to centrifugal force.

Where the scale model means is soil, the subjection of the scale model means to the centrifugal force has the effect of consolidating the soil. In such circumstances, in order to reproduce the effect of earthquakes, the soil may be subjected to shaking to provide shocks or vibrations, especially to provide a sinusoidal wave vibration.

Where the scale model means is liquid, it may be desirable to freeze the liquid; for example where the liquid is seawater, to freeze the seawater for so-called sea-ice work.

The scale model means advantageously extends completely or almost completely round the axis, so as to provide a large inwardly exposed area for simultaneous performance of a plurality of experiments.

According to a tenth aspect of the present invention, there is provided a centrifuge comprising a rotary wall having an outer periphery and rotatable about its own axis, rotary receiving means supported by said wall and located in the region of said outer periphery for receiving a sample to be tested, stationary means relative to which said wall and said receiving means are rotatable, and shaking means effective to produce shaking of said receiving means and thus said sample relative to said wall.

The shaking means may act between the stationary means and the receiving means. Moreover, the receiving means is advantageously distributed, if not continuous, round the axis, and the shaking means is advantageously distributed around, or continuous round, the axis.

Preferably, the receiving means is shakeable by some means, for example hydraulic ram means, acting between the receiving means and the rotary wall or drum. In order to reduce the effect of the shaking upon the rotary wall or drum and its bearing (s), the wall or drum should have a mass much larger than that of the sample to be tested. For this reason, the wall may be relatively massive.

According to an eleventh aspect of the present invention, there is provided a centrifuge comprising a rotary wall having an annular outer periphery and rotatable about its own axis, and rotary receiving means supported by said wall, located in the region of said outer periphery, and serving to receive a sample to be tested, said rotary wall being massive relative to said receiving means.

The relatively massive diametral wall has the advantage of stiffly resisting outward deflection of the receiving means under centrifugal force. It also has the advantage of reducing the effect upon the bearings(s) of any shaking of the sample.

According to a twelfth aspect of the present invention, there is provided a centrifuge comprising a rotary member rotatable about an axis, rotary receiving means carried by said member at a location spaced from said axis for receiving scale model means to be tested, first shaking means effective to produce shaking of said receiving means to-and-fro in a first sense, and second shaking means operable independently of said first shaking means and effective to produce shaking of said receiving means to-and-fro in a second sense transverse to said first sense.

Owing to this aspect of the invention, it is possible to model the actual wave pattern of a complex earthquake, since such earthquakes comprise waves transverse to each other and the phase relationship between the waves in one sense and the waves in the transverse sense may vary greatly from one earthquake to another. The centrifuge may be in the form of an arm or a drum. In practice, the first sense could be tangential and the second sense radial.

According to a thirteenth aspect of the present invention, there is provided a centrifuge comprising a rotary member rotatable about an axis, a plurality of rotary masses distributed around said axis and carried by said member, at least one of said masses comprising receiving means for receiving a sample to be tested, a plurality of shaking means distributed around said axis and acting between the respective masses, on the one hand, and said member, on the other hand, to produce shaking of the respective masses radially of said axis in such manner that the vector sum of the radial forces generated at the zone of said member at said axis by the radial shaking is substantially zero.

This aspect of the invention has the advantage of minimizing impact load on a rotary bearing for said member at said axis.

The plurality of shaking means may additionally produce shaking of the masses tangentially with respect to the axis in such manner that the vector sum of the tangential forces is reacted by the inertia of the rotary wall or drum.

According to a fourteenth aspect of the present invention, there is provided a centrifuge comprising a rotary wall having an annular outer periphery and rotatable about its own axis, rotary receiving means supported by said wall and located in the region of said outer periphery, and freezing means serving to freeze a liquid in said receiving means.

According to a fifteenth aspect of the present invention, there is provided a scale modelling centrifuge comprising a drum and upper and lower bearings at respective ends of said drum and mounting said drum for rotation about its longitudinal axis, which is substantially vertical.

Having bearings at both ends of the drum enables the speed of rotation of the drum to be higher than with only one bearing.

With such a centrifuge, access for an operator or materials to the interior of the drum may be obtained through the centre of one or both of the bearings.

Alternatively, in order to give very good access, the drum may include a detachable lid itself centrally mounted in the upper bearing.

The present scale modelling centrifuge including a substantially circular rotary wall or drum has the advantage over known scale modelling arm centrifuges that higher forces can be obtained. One reason for this is that the wall or drum has better aerodynamic properties than the arm, so permitting a greater speed of rotation of the wall or drum than of the arm. Another reason is that the wall or drum has better balancing properties than does the arm. We believe it to be possible with a drum to obtain values of at least 500 G with a tonne specimen, compared with the present commercially available arm centrifuges which attain values of up to about 200 G with a tonne specimen.

According to a sixteenth aspect of the present invention, there is provided a centrifuge comprising a rotary wall having an annular outer periphery and rotatable about an axis, rotary receiving means supported by said wall and located in the region of said outer periphery, stationary means relative to which the rotary wall is rotatable, instrumentation carried by said rotary wall, data processing means also carried by said rotary wall, slip ring means between said rotary wall and said stationary means, data utilizing means carried by said stationary means, and electrically conductive means connecting said instrumentation to said data utilizing means by way of said data processing means and said slip ring means, said data processing means serving to convert analogue electrical signals from said instrumentation into digital signals.

The conversion of the analogue signals into digital signals on the rotary wall has the advantage of mitigating the effect of signal distortions produced by electrical interference, which may be generated at such slip ring means. It also enables the number of slip rings and their associated electrical conductors to be minimized.

According to a seventeenth aspect of the present invention, there is provided a centrifuge including a rotary wall having an annular outer periphery and rotatable about its own axis and provided with an annular recess substantially co-axial with said wall and opening towards said axis, a sample carried by said rotary wall radially outwardly of said recess, a stationary conduit for supplying liquid to said recess, and duct means extending from said recess towards said sample for conducting said liquid under centrifugal force from said recess towards said sample.

According to an eighteenth aspect of the present invention, there is provided a centrifuging method, comprising providing a centrifuge including a rotary wall having an annular outer periphery and rotatable about its own axis, mounting a sample on said wall radially outwardly of an annular recess formed in said wall co-axially with said wall and opening towards said axis, and supplying liquid to said annular recess while said wall is rotating and thereby causing said liquid to flow under the action of centrifugal force from said recess through duct means to said sample.

This system provides a simple way of supplying liquid to a sample, without requiring the high standard of sealing necessary if using hydraulic slip rings, for example.

According to a nineteenth aspect of the present invention, there is provided a device for controlling liquid flow, comprising duct means for conducting liquid, and thermoelectric means in thermal communication with the interior of said duct means for producing cold in said interior to solidify said liquid therein.

According to a twentieth aspect of the present invention, there is provided a device for controlling hydraulic pressure in a container, comprising duct means for communicating with a region of the interior of said container at which the hydraulic pressure is exerted, and drive means which serves to displace an outlet end of said duct means selectively in a direction of increasing hydraulic pressure in said container or in the opposite direction.

According to a twenty-first aspect of the present invention, there is provided a method of controlling hydraulic pressure, comprising supplying liquid to a container, operating drive means to displace selectively in a direction of increasing hydraulic pressure in said container or in the opposite direction an outlet end of duct means communicating with a region of the interior of said container at which the hydraulic pressure is exerted.

Each of these systems is particularly useful for selectively preventing and allowing liquid flow in circumstances in which conventional on-off valves become unreliable, for example where the valves would have to operate under high pseudo-gravitational forces or where the liquid or particles therein may cause the valves to malfunction.

According to a twenty-second aspect of the present invention, there is provided consolidating apparatus, comprising a consolidation chamber for receiving a scale modelling sample to be consolidated, a movable wall of said consolidation chamber, a pressure chamber serving to receive a pressing fluid which presses said movable wall inwardly of said consolidation chamber, and mechanical means serving to apply a force to said fluid in said pressure chamber to pressurize said fluid.

This arrangement has the advantage of avoiding any need for the pressing fluid to be continually connected to a supply of pressing fluid.

According to a twenty-third aspect of the present invention, there is provided consolidating apparatus, comprising an annulus bounding peripheral channel means open towards the axis of the annulus for receiving a sample to be consolidated, and movable wall means arranged around said axis inwardly of said peripheral channel means and serving to press radially outwardly on said sample to consolidate the same.

This apparatus is particularly suitable for providing consolidated samples for circular centrifuges.

BRIEF DESCRIPTION OF DRAWINGS

In order that the invention may be clearly understood and readily carried into effect, reference will now be made, by way of example, to the accompanying drawings, in which.

MODES FOR CARRYING OUT THE INVENTION

Figure 1:
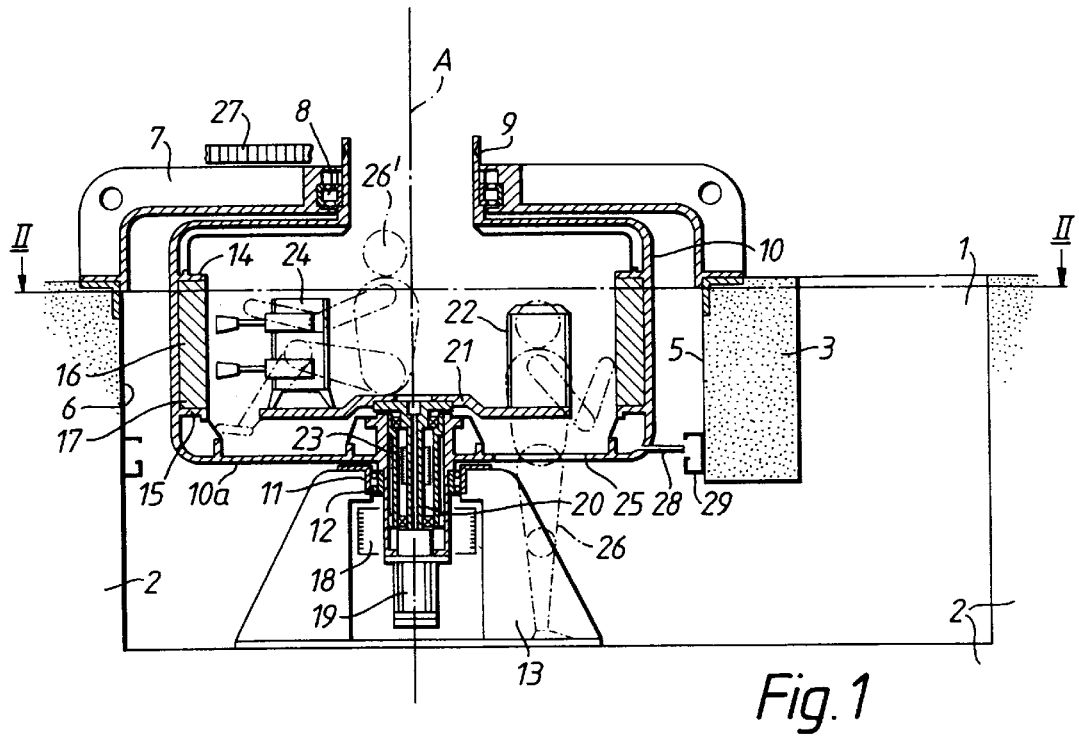
FIG. 1 is a vertical axial section through a geotechnical drum centrifuge.
Figure 2:
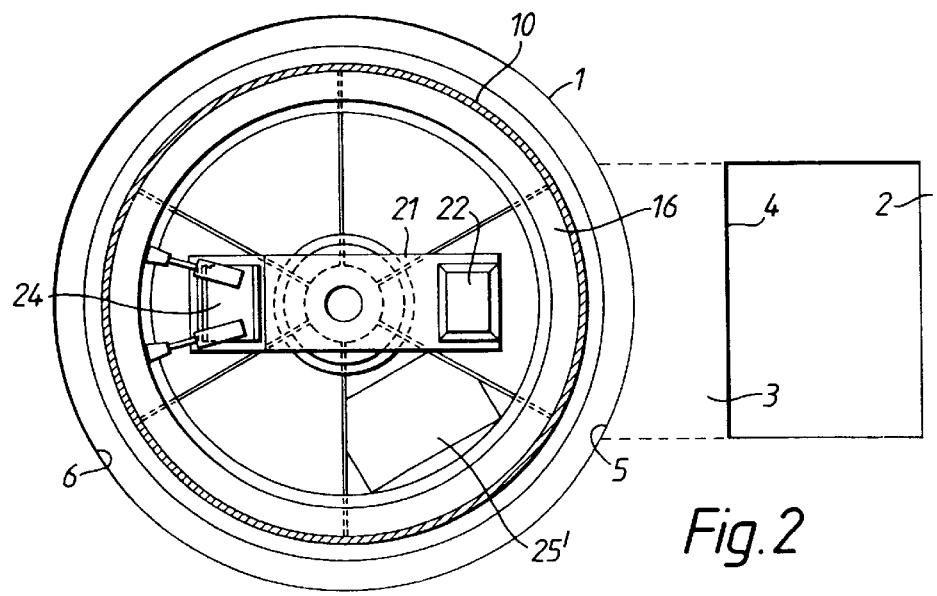
FIG. 2 shows a sectional plan view along the line II—II in FIG. 1.

Referring to FIGS. 1 and 2, the centrifuge comprises a keyhole-shaped pit 1 heavily lined with steel-reinforced concrete 2, with a steel-reinforced concrete arch 3 having a planar vertical face 4 and an arcuate vertical face 5 co-cylindrical with the cylindrical face 6 of the pit 1. The cylinder bounded by the faces 5 and 6 is substantially closed at its top by a rigid, annular, steel cap 7 solidly mounted at its outer, lower rim in the concrete 2. At its upper, inner rim, the cap 7 mounts a roller bearing 8 having a vertical axis A. Mounted co-axially in the bearing 8 is a stub tube 9 forming part of a container or drum 10 which also includes a coaxial stub tube 11 at its lower end. The stub tube 11 is mounted in a self-aligning barrel bearing 12 mounted securely in a heavy steel mounting 13 coaxial with the drum 10 and firmly fixed in the concrete 2 at the bottom of the pit 1. Fixed to an internal peripheral surface of the drum 10 coaxially with the drum 10 are upper and lower annular flanges 14 and 15 bounding between them an annular channel 16. Shown in the channel 16 is a scale modelling sample 17, in this instance soil, containing various detecting devices (for pressure, displacement, et cetera) electrically connected by leads to some of slip rings 18 fixed to the mounting 13. Mounted centrally of the mounting 13 is an electric motor 19 which drives a vertical shaft 20 co-axial with the drum 10 and fixed at its upper end to a work support in the form of a turntable 21. Various detecting devices carried by the turntable 21 are connected, if desired by way of a control box 22, to slip rings 23 themselves electrically connected via leads to some of the slip rings 18. Shown mounted on the turntable 21 is a testpiece 24 simulating the legs of an off-shore platform. Formed in the bottom wall 10a of the drum 10 is a manhole 25 with a cover 25' through which manhole an operator may gain access to the interior of the drum 10 from below the drum. Such operator is diagrammatically indicated at 26. The bottom wall 10a of the drum 10 is spaced from the floor of the pit 1 sufficiently that the operator 26 may enter the manhole 25 from below and, as shown, have the upper part of his body at a level suitable for him to work upon the sample 17 present in the channel 16, while standing on the bottom of the pit 1. The bottom wall of the drum 10 is at approximately the height of the hips of the operator 26. If desired, the operator may enter the drum 10 by way of the interior of the stub tube 9. The operator 26 is shown at 26' seated upon the turntable 21. There may be more than one manhole provided in the bottom wall of the drum 10. A drive belt 27 is used to drive the stub tube 9 and thus the drum 10 about the axis A. In order to drain liquid from the drum 10, at least one drain pipe 28 extends to an annular drain conduit 29 fixed to the surfaces 5 and 6.

In use, while the drum 10 is spinning, soil to be tested may be introduced through the stub tube 9 and laid in the channel 16, for example via a flexible hose (not shown). Rotation of the drum 10 about its axis A is used to produce consolidation of the soil. The continuous internal annular face provided by the cap 7 and the continuous annular face provided by the surfaces 5 and 6 discourage turbulence in the air adjacent to the drum 10 and thus facilitate the achievement of relatively high speeds of rotation of the drum.

Figure 3:
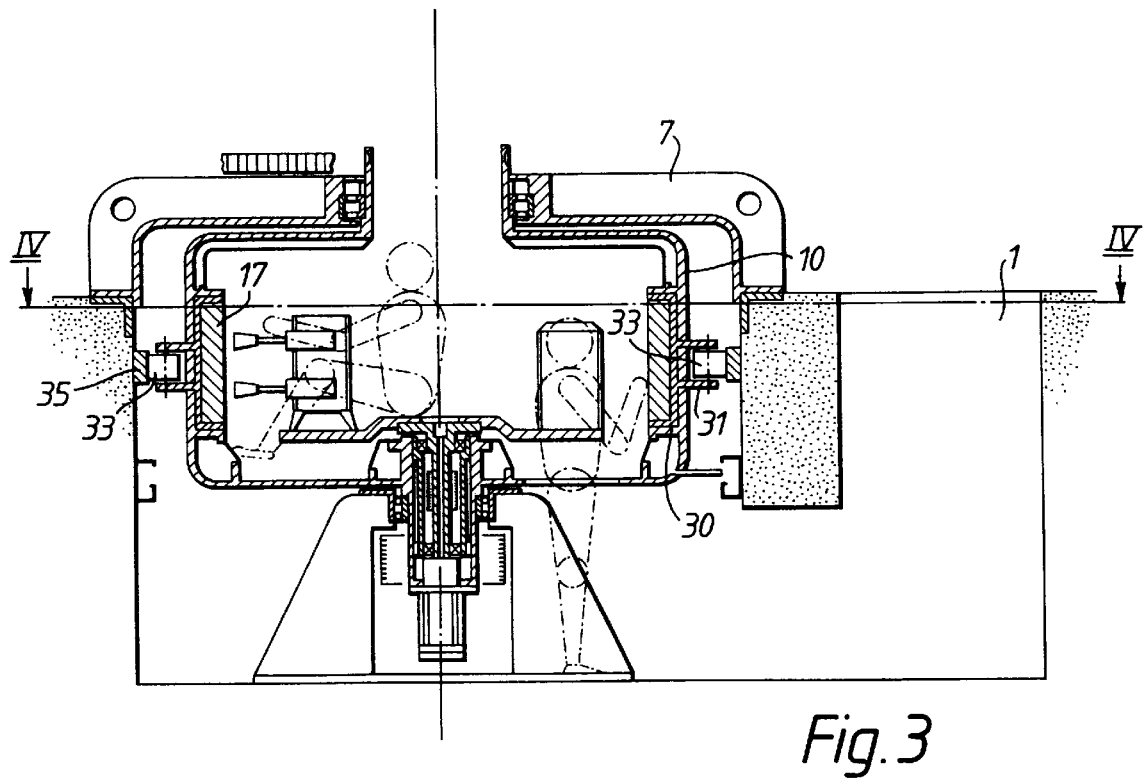
FIG. 3 is a view similar to FIG. 1 of a modified version of the drum centrifuge.
Figure 4:
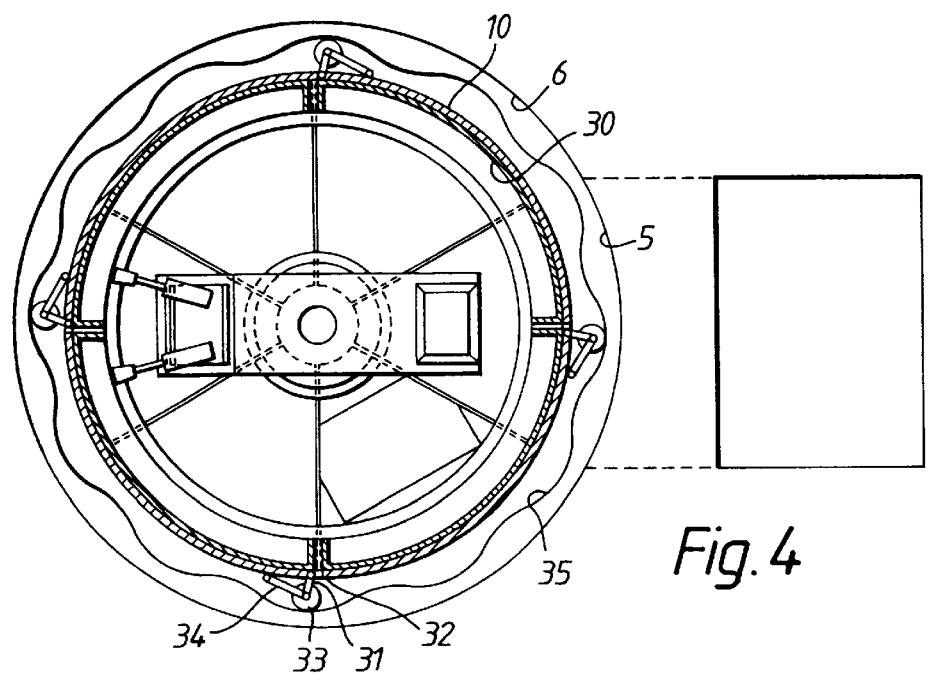
FIG. 4 is a view similar to FIG. 2 taken on the line IV—IV in FIG. 3.

Referring to FIGS. 3 and 4, the version shown therein differs from the version shown in FIGS. 1 and 2 in that the annular channel 16 receives a plurality of arcuate troughs 30 which are connected via respective links 31, passing through respective circumferential slots 32 in the peripheral wall of the drum 10, to respective rollers 33 connected to that wall of the drum 10 by way of respective links 34. The links 31 are articulated to the troughs 30 and to the rollers 33, whilst the links 34 are articulated to the rollers 33 and the drum 10. Another difference is that the annular face provided by the surfaces 5 and 6 has fixed thereto a cam track 35 of a sinusoidal form. The purpose of the cam track 35 and the rollers 33 is to cause the troughs 30 to perform a sinusoidal wave motion to simulate the effect of an earthquake in the soil 17 in the troughs 30. The rollers 33 follow the sinusoidal surface of the track 35 under centrifugal force as the drum 10 is rotated, oscillating radially under the control of the links 34. By way of the links 31 they push the troughs 30 tangentially relative to the drum 10, so imparting a circumferential oscillation to the system of troughs 30 to simulate the effect of an earthquake. The items 30 to 35 are all demountable and removable from the centrifuge in order that it can be used for the type of testing illustrated in FIGS. 1 and 2.

Figure 5:
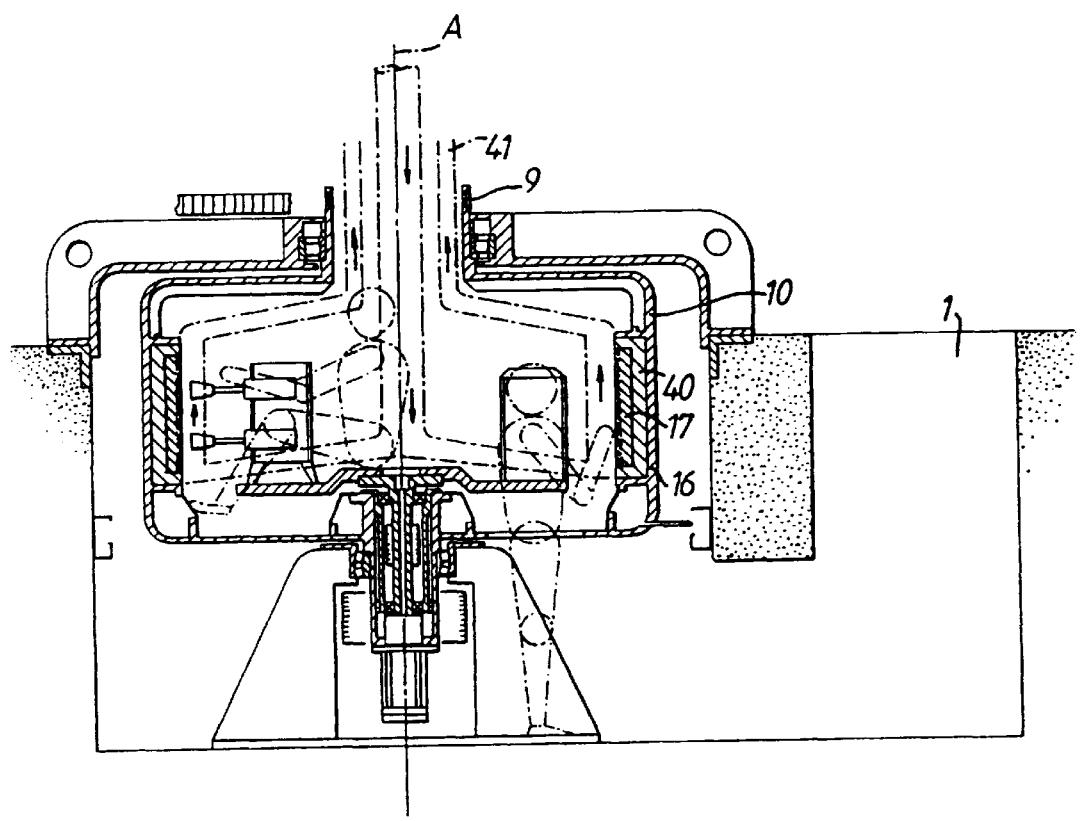
FIG. 5 is a view similar to FIG. 1 showing another modified version of the centrifuge.

The version shown in FIG. 5 differs from that shown in FIG. 1 in that the scale modelling sample 17 is in the form of seawater carried in an annular channel 40 of thermal insulation itself fitting in the annular channel 16.

Again, in order to introduce the liquid 17 into the channel 40, the drum 10 is spun about its axis A and the seawater 17 supplied to the channel 40 by way of a flexible hose (not shown) introduced through the stub tube 9. If it is desired to freeze the exposed surface 17' of the liquid 17, a cryogenic duct system 41 may be arranged in the drum 10 to feed a freezing gas or liquid to immediately adjacent to the seawater 17 to freeze the same.

Figure 6:
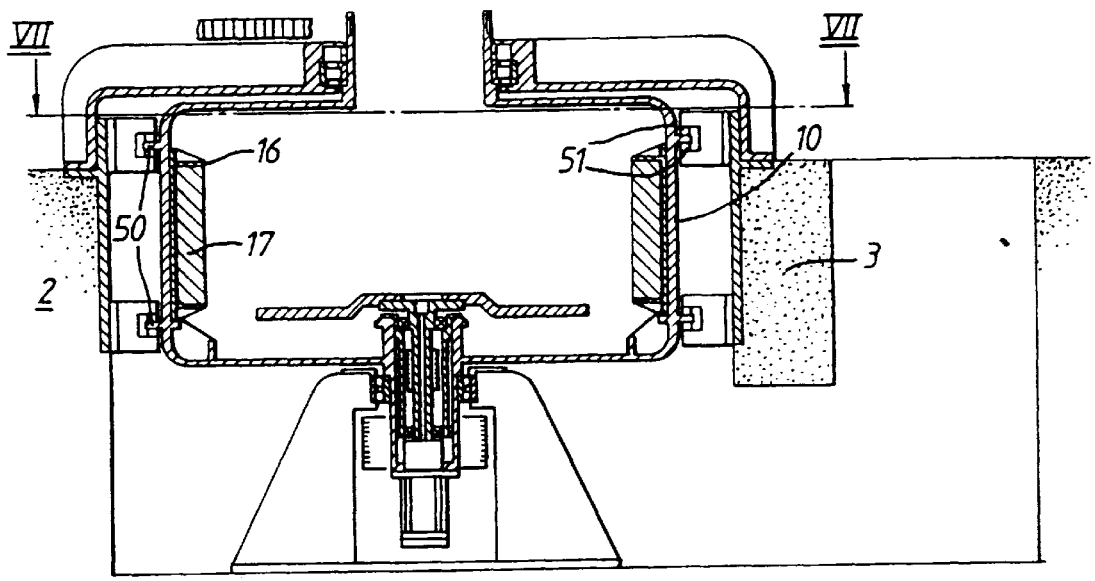
FIG. 6 is a view similar to FIG. 1 of a third modified version of the centrifuge.
Figure 7:
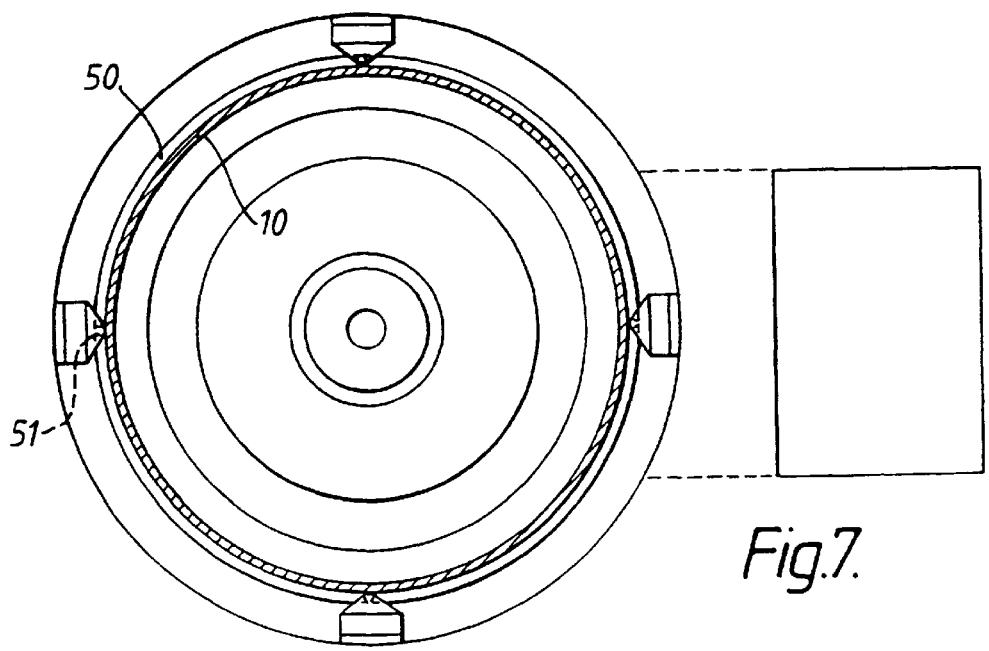
FIG. 7 is a view similar to FIG. 2 taken on the line VII—VII of FIG. 6.

The version shown in FIGS. 6 and 7 differs from that shown in FIGS. 3 and 4 mainly in that the earthquake-simulating system 30-35 is replaced by an earthquake-simulating system comprised of the annular channel 16 for containing the soil 17, horizontal, annular brake flanges 50 of the drum 10, and pairs of hydraulically-operated brake shoes 51 regularly spaced around the periphery of the drum 10 and mounted on the steel-reinforced concrete 2, 3. Pulsed application of the brake shoes 51 to the flanges 50 produces an earthquake effect circumferentially in the soil 17.

Figure 8:
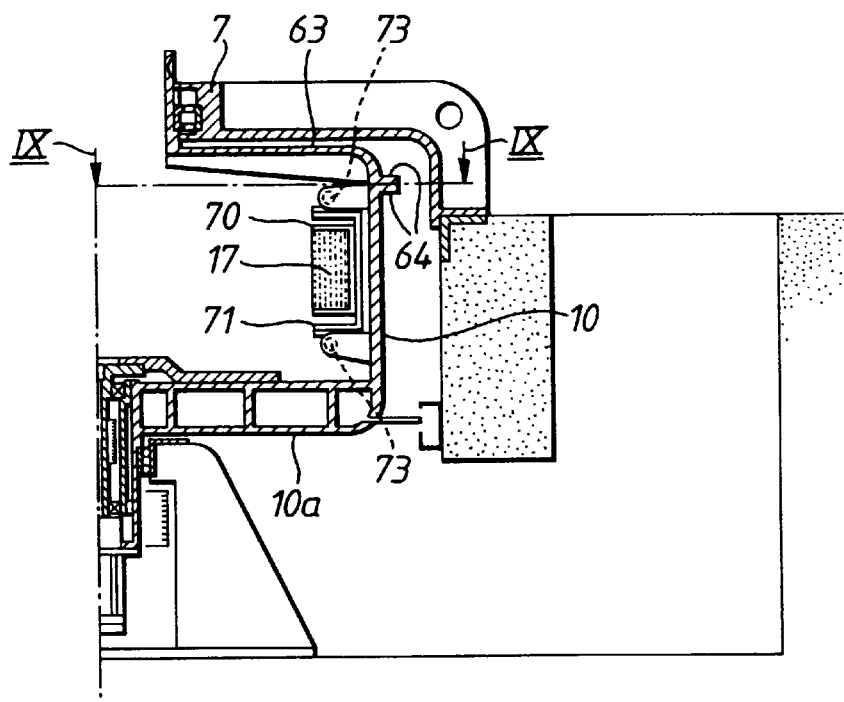
FIG. 8 is a half-view of a vertical axial section through a fourth modified version of the centrifuge.
Figure 9:
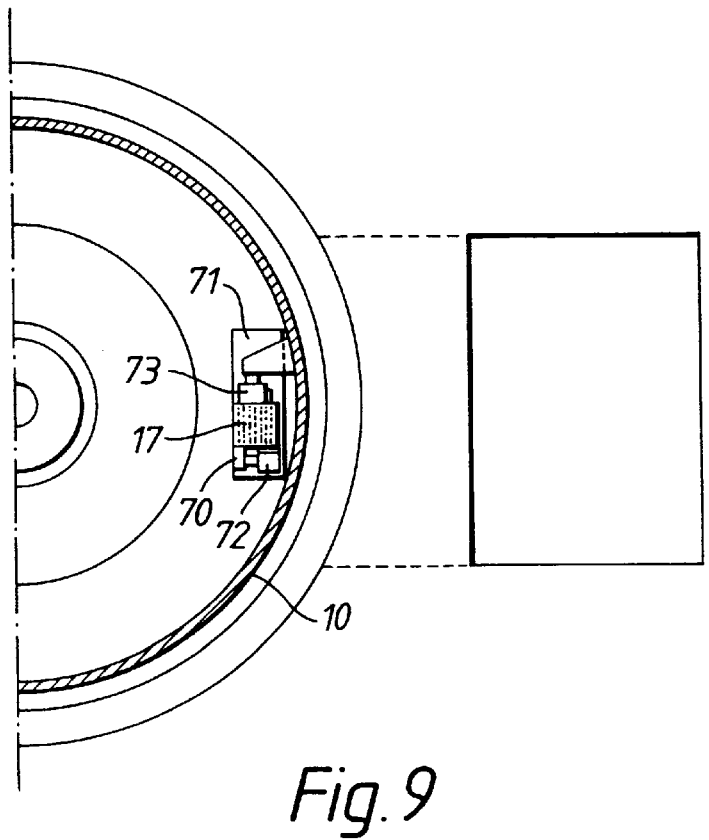
FIG. 9 is a half-view of a sectional plan taken mainly on the line IX—IX in FIG. 8.
Figure 8A:
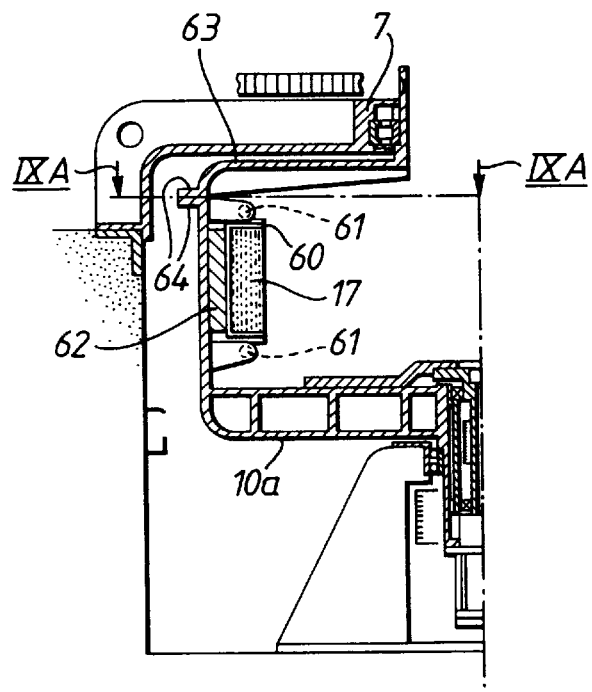
FIG. 8A is a half-view of a vertical axial section through a fifth modified version of the centrifuge.
Figure 9A:
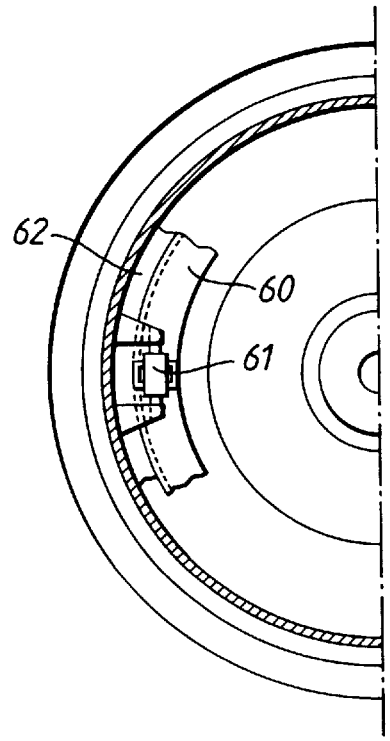
FIG. 9A is a half-view of a sectional plan taken mainly on the line IXA—IXA of FIG. 8A.

There are two versions shown in FIGS. 8 and 9, and 8A and 9A. Two main differences between the versions shown in FIGS. 8 and 9 and the versions shown in FIGS. 3, 4, 5 and 6 are that, firstly, the bottom wall 10a of the drum 10 is of a relatively massive construction (and without an access such as the manhole 25) and, secondly, the earthquake-simulating system is contained within the drum 10. In FIGS. 8A and 9A is shown a system in which the soil 17 is contained in an annular channel 60 mounted between pairs of upper and lower hydraulic rams 61 operating circumferentially of the drum 10. An elastomeric annulus 62 may be interposed between the channel 60 and the internal peripheral surface of the drum 10 to support the channel 60 radially relative to the drum 10.

The relatively massive bottom wall of the drum 10 gives the drum 10 a relatively high reaction mass to minimize transmission through the drum of the circumferential oscillation motions produced by the rams 61. The drum 10 includes a lid 63 bolted at flanges 64 to the remainder of the drum 10 and centrally including the stub tube 9 mounted in the bearing 8. Following removal of the steel cap 7, the lid 63 is readily removable to give very good access to the interior of the drum 10.

The relatively massive bottom wall also provides strength to react local forces that may be applied to the wall.

In FIGS. 8 and 9 is shown a system in which the soil 17 is contained in a trough 70 mounted within a trough 71 by way of a pair of hydraulic rams (of which one is seen and referenced 72) arranged to oscillate the trough 70 radially relative to the trough 71. The trough 71 is itself mounted upon the internal peripheral surface of the drum 10 by way of pairs of upper and lower hydraulic rams 73 acting circumferentially of the drum. The rams 72 and 73 can be programmed to operate independently of each other simultaneously to impart to the soil 17 oscillations in two senses (namely radially and circumferentially, respectively, of the drum) substantially perpendicular to each other. The programme can be such that the rams operate in phase relationship the same as that of the earthquake wave pattern which it is desired to simulate. The assembly 17,71-73 is one of at least two equal masses mounted upon and regularly distributed around the internal peripheral surface of the drum to ensure dynamic and static balance of the drum about its axis, whereby the vector sum of forces at the centre of the drum will be zero. The sub-assembly 17,70 is one of a corresponding number of equal sub-masses included in the equal masses. These sub-masses are so oscillated radially of the drum 10 by pairs of rams (72) that the vector sum of the radial forces at the centre of the drum 10 will be zero.

In FIGS. 10 and 10A and 11 and 11A the centrifuge is relatively small and the bottom bearing 12 in FIG. 1 has been replaced by a pair of bearings 87 and 88 which can resist moments. This small drum is capable of operation at a useful speed without the assistance of an upper bearing. The relatively massive base wall in the form of a diametral plate 80 now carries a detachable peripheral wall 81 of the drum 10, together with a lid 82 closing the interior space 86 within which the scale modelling sample(s) 17 is/are placed.

Figure 10:
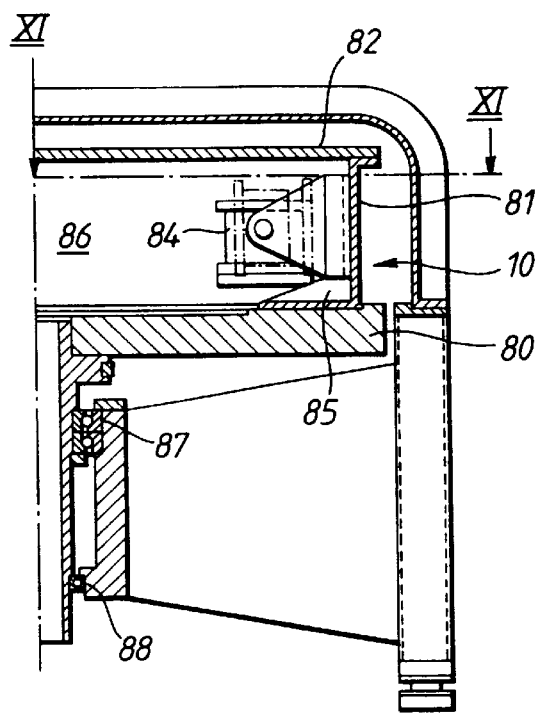
FIG. 10 is a view similar to FIG. 8 of a sixth modified version of the centrifuge.
Figure 11:
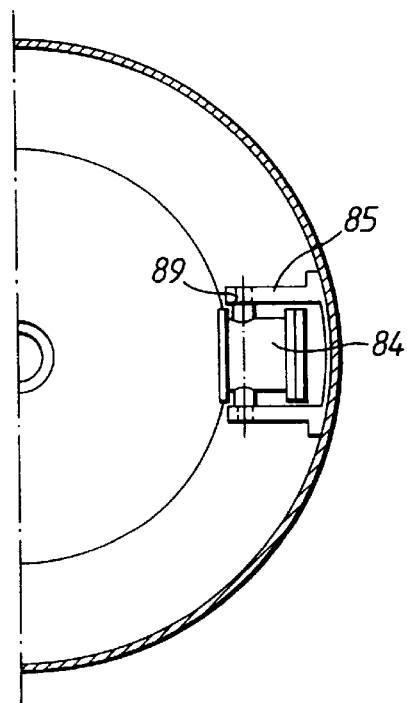
FIG. 11 is a view similar to FIG. 9 taken mainly on the line XI—XI in FIG. 10.
Figure 10A:
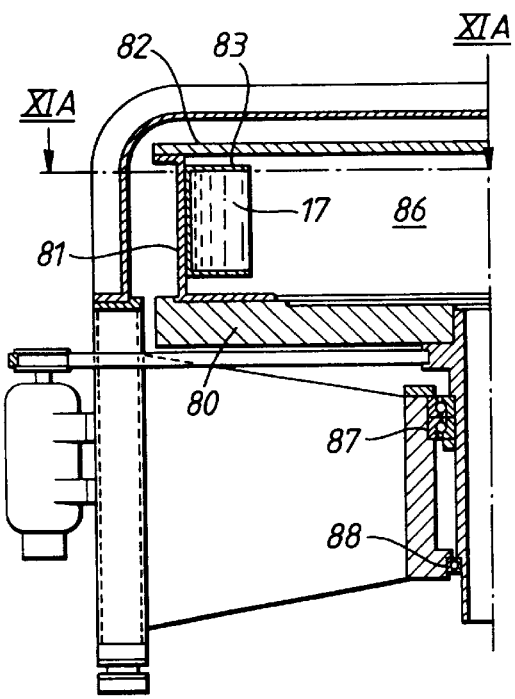
FIG. 10A is a view similar to FIG. 8A of a seventh modified version of the centrifuge.
Figure 11A:
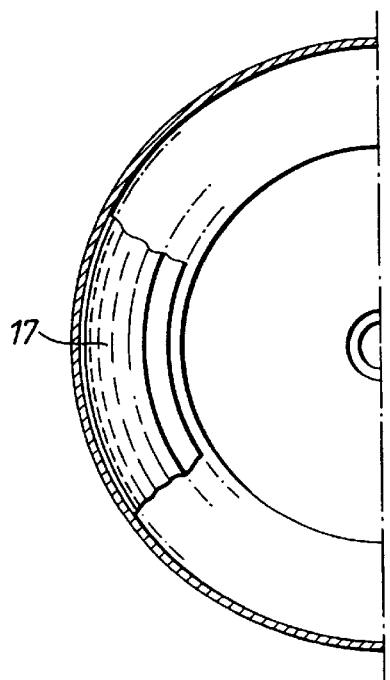
FIG. 11A is a view similar to FIG. 9A taken mainly on the line XIA—XIA of FIG. 10A.

In FIGS. 10A and 11A is shown a section of a ring channel 83, within which the sample 17 can be mounted, located above the plate 80. In FIGS. 10 and 11 is shown an individual sample container 84 in a gimbal mounting 89, which is an alternative way of mounting a geotechnical sample. The strength and stiffness of the plate 80 is adequate to support the bracket system 85 secured to the plate 80. The mounting 89 allows the container 84 to swing to an angle determined by the mass and the speed of rotation. Alternatively, the container 84 can be fitted without the use of a pivot mounting. One or more appropriate counterweights can be mounted on one or more bracket systems at the opposite side of the plate 80 if required.

As in FIGS. 8 and 9, and 8A and 9A, it is also possible to apply earthquake forces and react these forces by applying loads to the plate 80.

In FIG. 10 or 10A it is also possible to incorporate a central platform 21 as shown in FIG. 1.

In FIG. 12 the centrifuge is again relatively small but the sample 17 has been made relatively high. In such circumstances, it is appropriate to reintroduce the top bearing 91. There is an extension section 92 to the peripheral wall of the drum and a stiff holder 93 with a stiff lid 94 and a stiff stub axle 95, the holder 93 serving to receive the sample 17. This stub axle 95 is supported by a self-aligning bearing 96 mounted in the cap 90.

Figure 12:
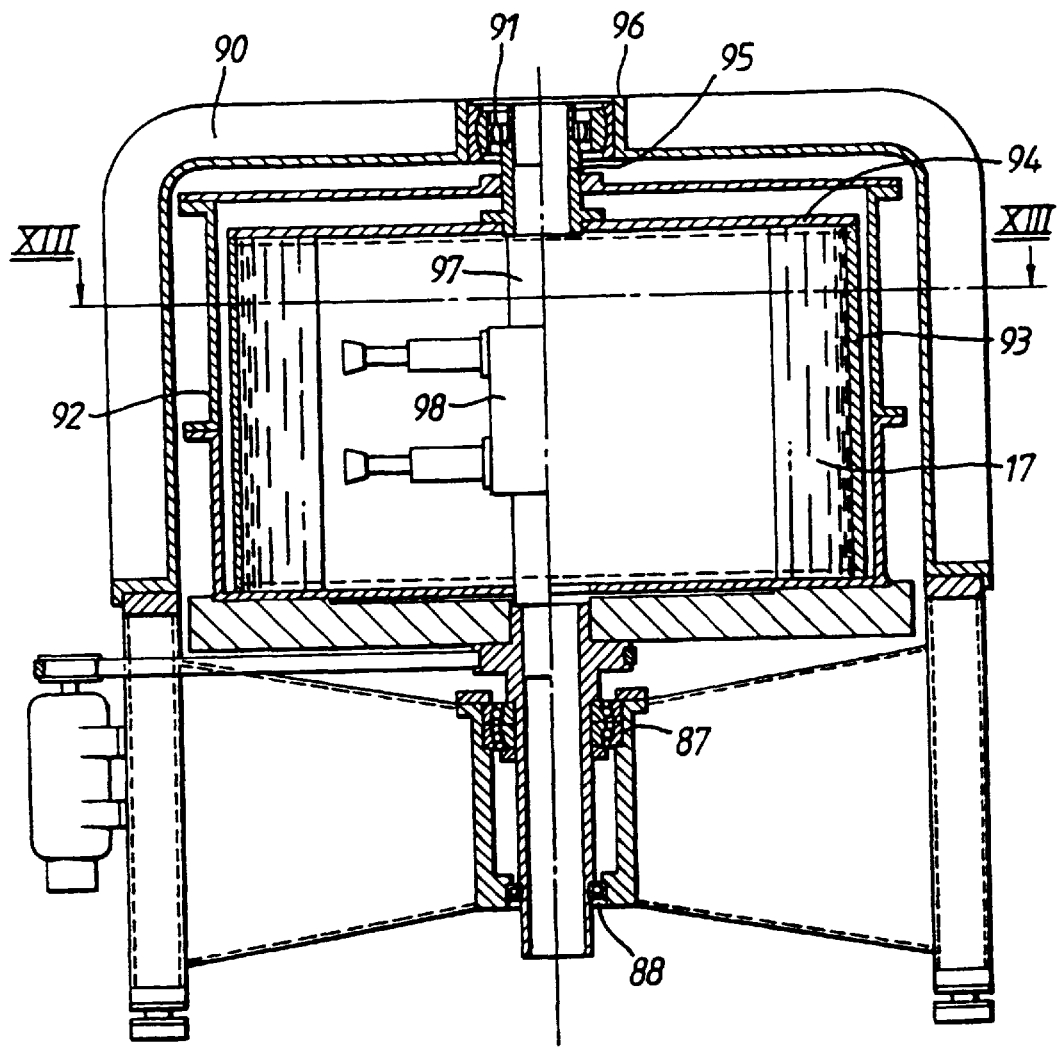
FIG. 12 is a view similar to FIG. 8 of eighth and ninth modified versions of the centrifuge.
Figure 13:
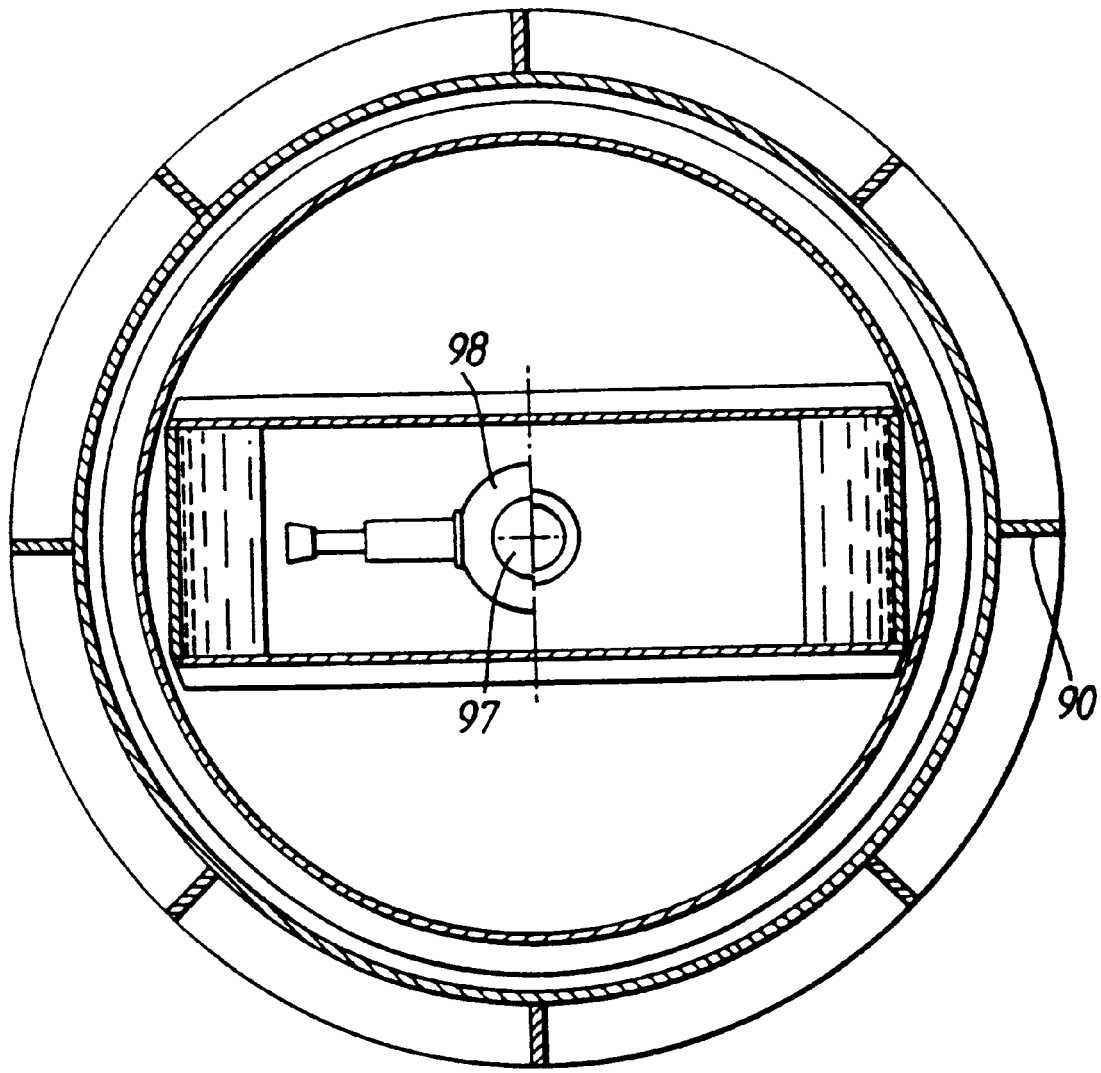
FIG. 13 is a view similar to FIG. 9 taken mainly on the line XIII—XIII in FIG. 12.

In FIGS. 12 and 13 on the left-hand side is shown a central work steady or mandrel 97. This mandrel 97 is mounted between the upper bearing 91 and the lower bearing 87 and provides a stiff mounting for a work support 98. A range of tools and/or experimental equipment can be mounted on the support 98, permitting the movement of equipment relative to the sample 17.

In order that a number of scale modelling samples may conveniently be prepared away from the drum and then tested in sequence (for example where a small drum centrifuge is used for teaching a laboratory class) a variety of consolidometers may be used, such as are shown in FIGS. 14 to 17.

Where geotechnical material such as clay is tested, the samples may require many days of preparation in consolidometers. The use of consolidometers considerably improves the utilisation of centrifuges in that samples are consolidated without the need to operate a centrifuge for prolonged periods.

Figure 14:
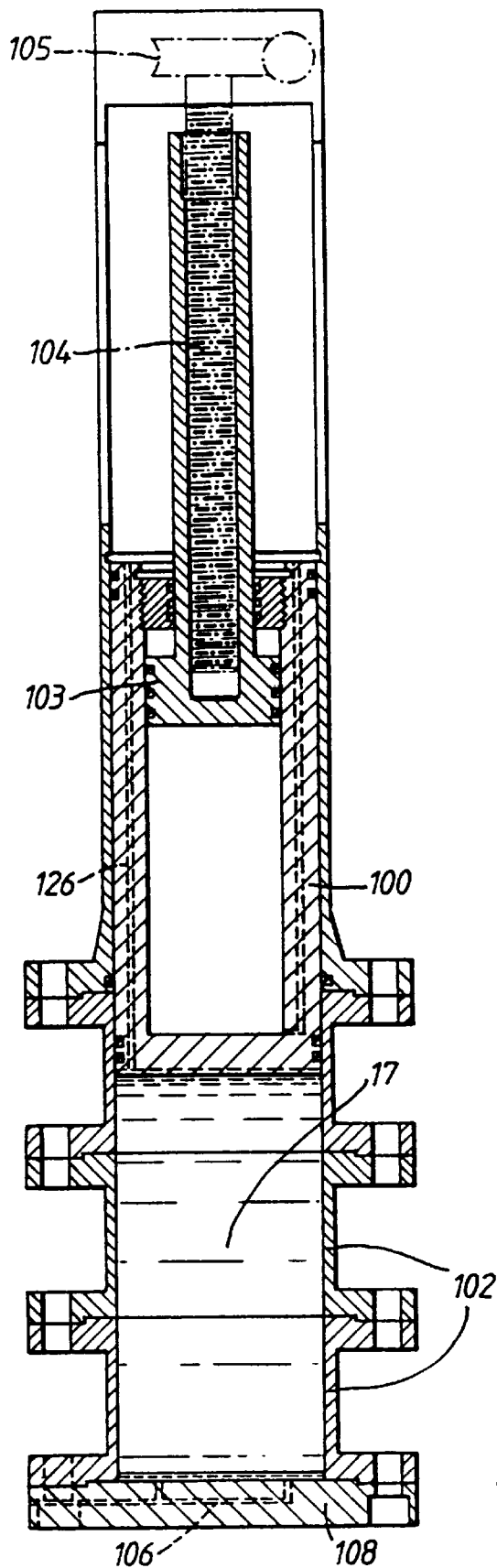
FIG. 14 shows a vertical axial section through a consolidometer for producing geotechnical samples for, e.g., the seventh modified version shown in FIGS. 10 and 11.

FIG. 14 shows a consolidometer for the compaction of a circular-cylindrical sample 17. Gas, for example air, is contained in the cylinder 100; this air may be at a pressure of greater than 1 BAR. The pressure exerted by the air reacts against a piston 103 to exert a force on the movable cylinder 100 and thus on the sample 17 which is contained by sample cylinders 102 and a base 108.

The piston 103 is driven down, to compress the air, by a screw 104 which is actuated by a worm-and-wheel 105. The worm may be turned by powered means or manually. Turning of the worm will cause changes in pressure in the cylinder 100 and thus on the sample 17. If the worm is powered, an automatic system of sensing the air pressure can be introduced, permitting the air pressure to be "topped-up" when necessary, or permitting the pressure to be programmed to a set sequence.

During consolidation, water in the sample can drain through ducts 106 in the base 108.

Figure 15:
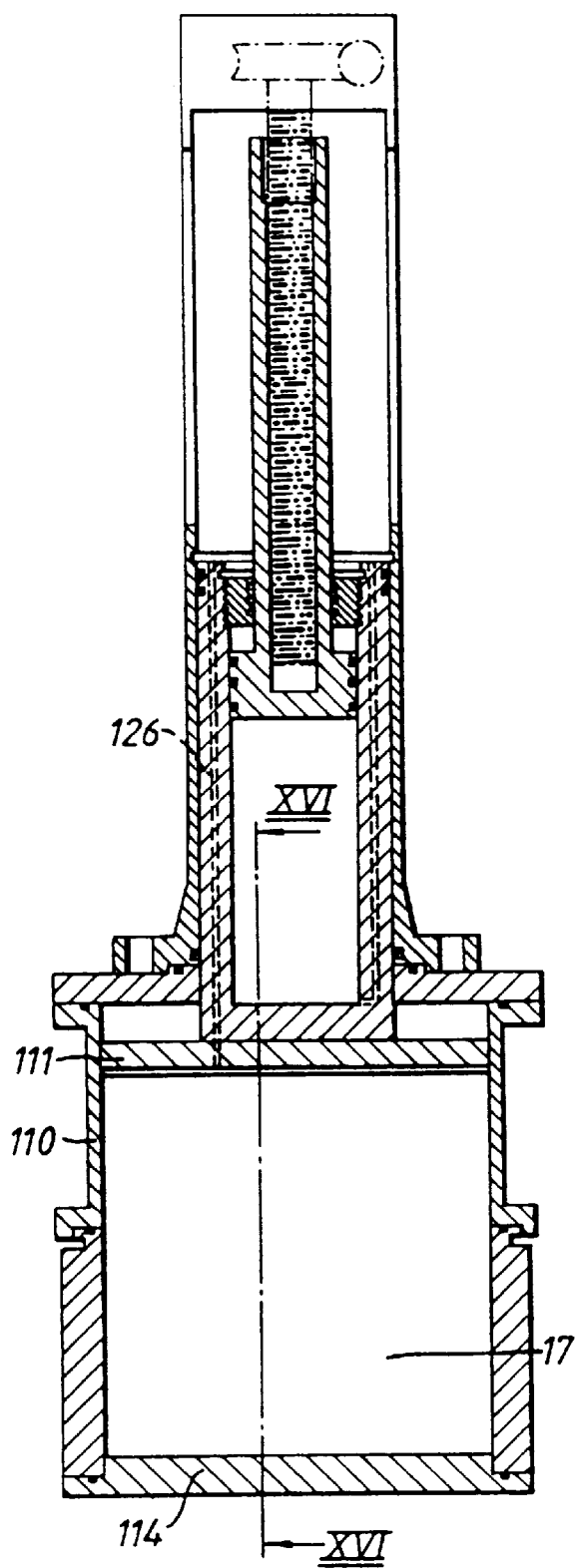
FIG. 15 is a view similar to FIG. 14 of a modified version of the consolidometer.
Figure 16:
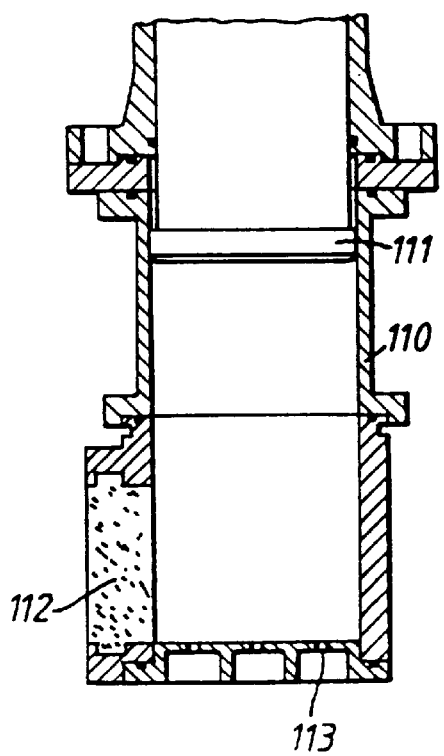
FIG. 16 is a fragmentary section taken on the line XVI—XVI of FIG. 15.
Figure 17:
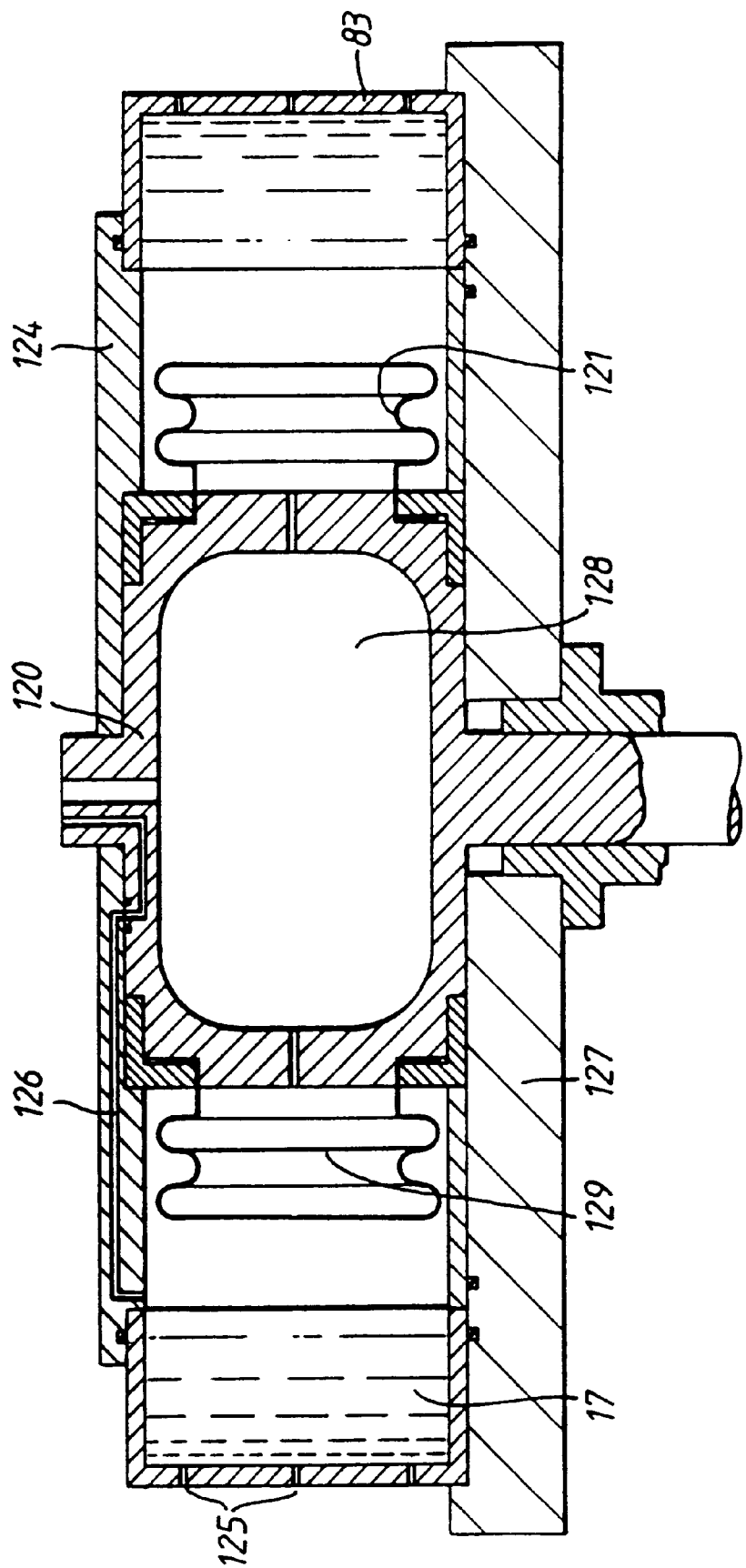
FIG. 17 shows a vertical axial section through a consolidometer for producing geotechnical samples for, e.g., the modified versions shown in FIGS. 12 and 13.

FIGS. 15 and 16 show a consolidometer in which the sample 17 is held in a container 110 which is of rectangular cross-section. The system for consolidating the sample is similar to that of FIG. 14, except that a piston plate 111 is rectangular. One side of the container 110 includes a transparent viewing panel 12. This panel permits the viewing of the specimen during consolidation and during test on a centrifuge. In-flight viewing (with the centrifuge rotating) may be achieved by a variety of means including stroboscopic illumination, closed circuit television with rugged cameras, and short duration flash illumination synchronised with a stationary camera located adjacent the centrifuge.

Where a sample 17 is to be consolidated into a ring channel 83, as shown in FIGS. 10 and 11, or 10A and 11A, for example, it is appropriate to have a circular consolidation press as shown in FIG. 17. In this press, there is a central cylinder 120 and an inflatable elastomeric tubular member 121 encircling the central cylinder 120. The ring channel 83 is placed on a support table 127 which also locates the central cylinder 120. The sample 17, for example a clay slurry, is poured into the channel and sealed with a cover plate 124.

A fluid under pressure is fed into the inner chamber 128 and creates a pressure within the annular interior 129 of the elastomeric member 121. This pressure acts upon the sample 17 and over a period of time the sample will be consolidated.

Holes 125 in the periphery of the channel 83 allow for the drainage of water from the sample. By feeding water under pressure through one or more ducts 126 into the sample, a downward hydraulic gradient can be achieved during consolidation.

With the consolidometers shown in FIGS. 14, 15 and 16, this downward hydraulic gradient is also obtainable using the ducts 126. The application of downward hydraulic gradient produces a softness of the sample at its upper or inner face at which the hydraulic pressure is applied directly to the pores of the sample. The sample will automatically be stiffer at its outer or lower face at which hydraulic flow drains to a lower pressure.

Figure 18:
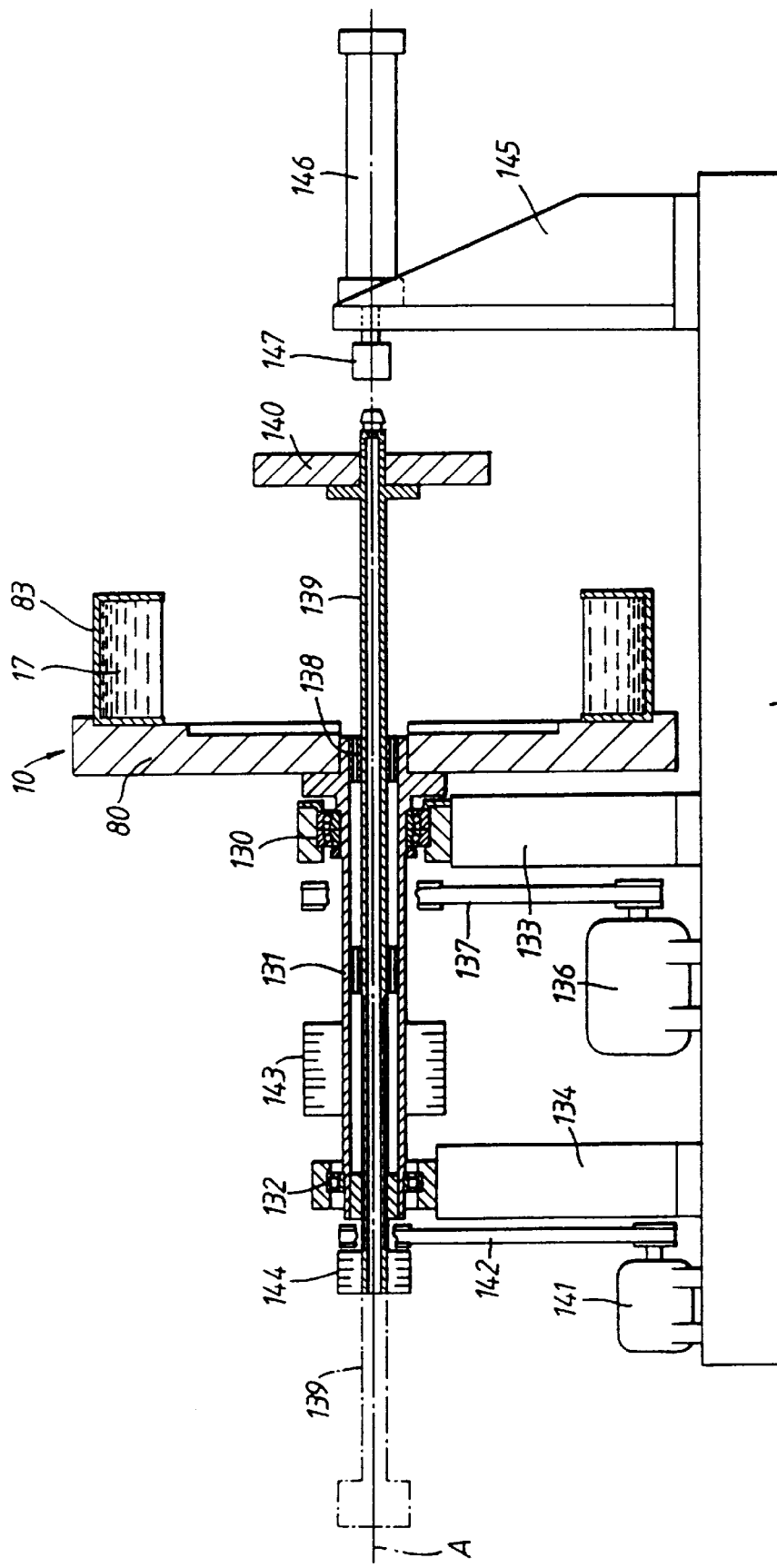
FIG. 18 shows a vertical axial section through a tenth modified version of the centrifuge.

FIG. 18 shows a drum centrifuge in which the drum 10 consists of the plate 80 and the detachable ring channel 83 and rotates about a horizontal axis A which is also its longitudinal axis. The drum 10 is mounted by way of a hollow axle 131 in horizontal bearings 130 and 132 carried by respective pillars 133 and 134 mounted upon a massive plinth 135. The hollow axle 131 and thus the drum 10 are rotated by an electric motor 136 via a belt-and-pulley system 137. Mounted horizontally and coaxially within the axle 131 by way of bearings 138 is a horizontal shaft 139 carrying a work support 140. The shaft 139 and thus the work support 140 are rotatable about the horizontal axis A by an electric motor 141 through a belt-and-pulley drive 142. Fixed to the axle 131 and the shaft 139 are respective sets of slip rings 143 and 144 whereby control et cetera signals may be transmitted to and from the rotating sample(s) 17 and the apparatus on the rotating work support 140. Fixed to the plinth 135 is a bracket 145 carrying a horizontal hydraulic ram 146 provided at its leading end with a latch device 147 for releasably seizing the adjacent end of the shaft 139, whereby the ram 146 may displace the shaft 139 and the work support 140 to-and-fro between a retracted position shown in full lines, in which the apparatus upon the support 140 is readily accessible, and a position shown partially in dot-dash lines, in which the work support 140 is received within the drum 10. The shaft 139 and the work support 140 can be retracted even while the drum 10 is still being rotated by the motor 136, although the motor 141 would be stopped prior to such retraction.

Figure 19:
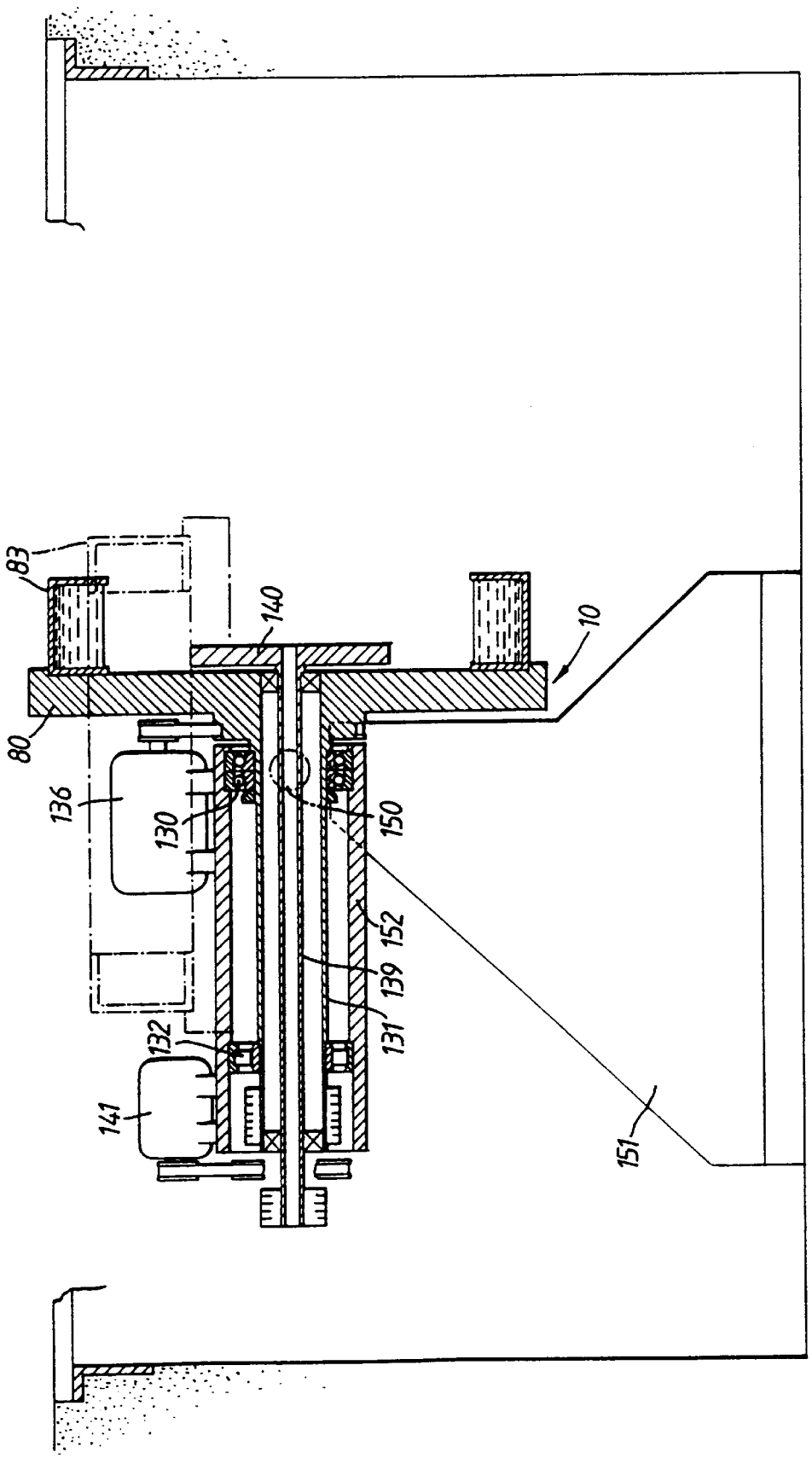
FIG. 19 is a view similar to FIG. 18 of an eleventh modified version of the centrifuge.

The major difference between the version shown in FIG. 18 and the version shown in FIG. 19 is that the centrifuge is turnable between the horizontal position shown in full lines in FIG. 19 and the vertical position shown in dot-dash lines therein, about horizontal trunnions 150 mounted in a massive bracket 151. This enables the user to obtain relatively easy access horizontally to the drum 10 and the work support 140 during construction of models and then to tilt the centrifuge into a vertical position to avoid during centrifuging the fluctuations in g force which would occur during rotation of the drum 10 about a horizontal axis. The trunnions 150 project from respective opposite sides of a sleeve 152 supporting the motors 136 and 141 and the axle 131.

Figure 20:
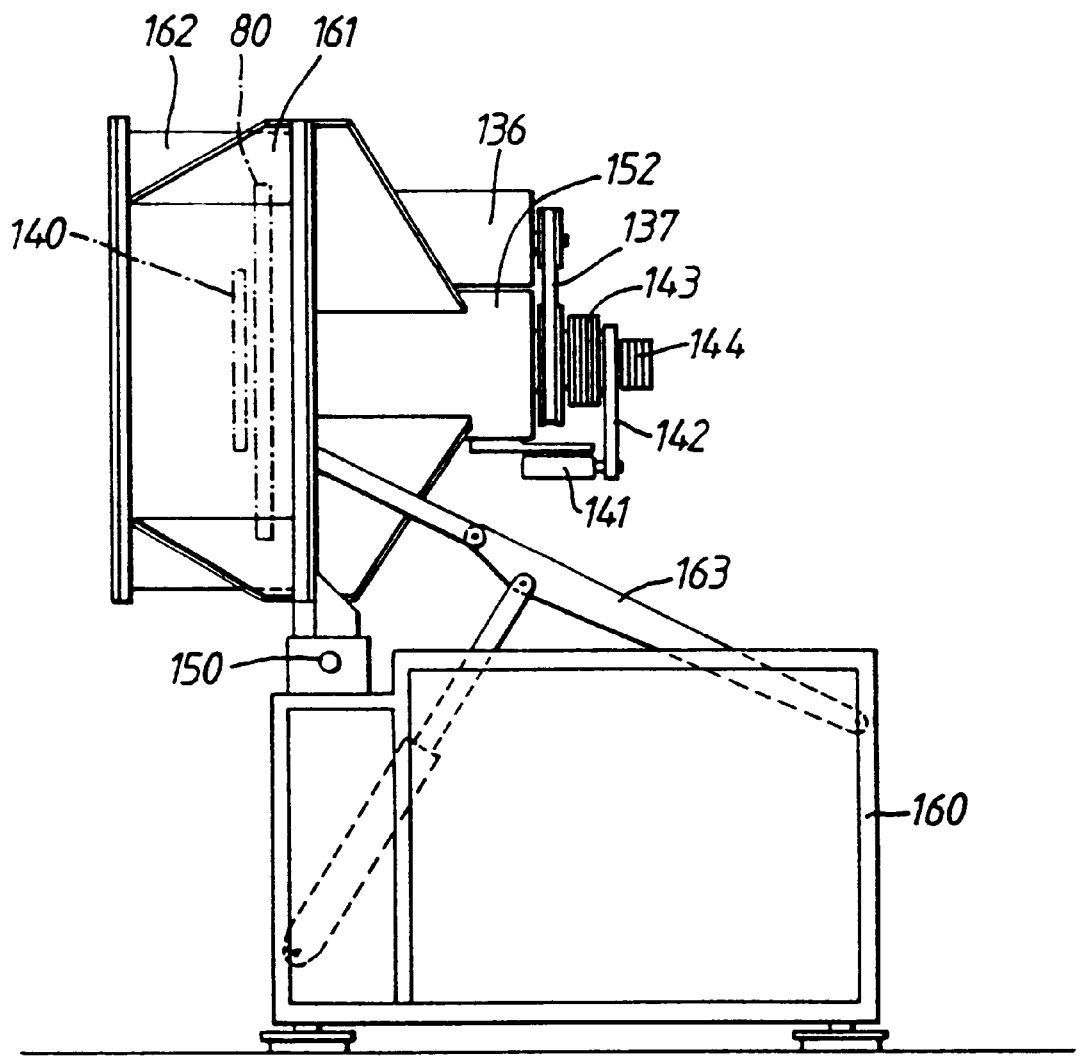
FIG. 20 shows a side elevation of a twelfth modified version of the centrifuge.

The major difference between the version shown in FIG. 19 and the version shown in FIG. 20 is that the centrifuge is free-standing and smaller. It includes a support stand 160 upon which is turnably mounted via the trunnions 150 a casing 161 including the sleeve 152 and a shroud 162 which serves to encircle the drum and thereby protect the operators. A ram-operated linkage 163 acting between the stand 160 and the casing 161 is used to turn the casing between the horizontal position shown, in which the operator has relatively easy access to the drum and the support 140, and a vertical position (not shown) in which the drum can be rotated at very high speed about its vertical axis, a safety interlock device (not shown) preventing rotation of the drum in its horizontal position except at slow speed.

Figure 22:
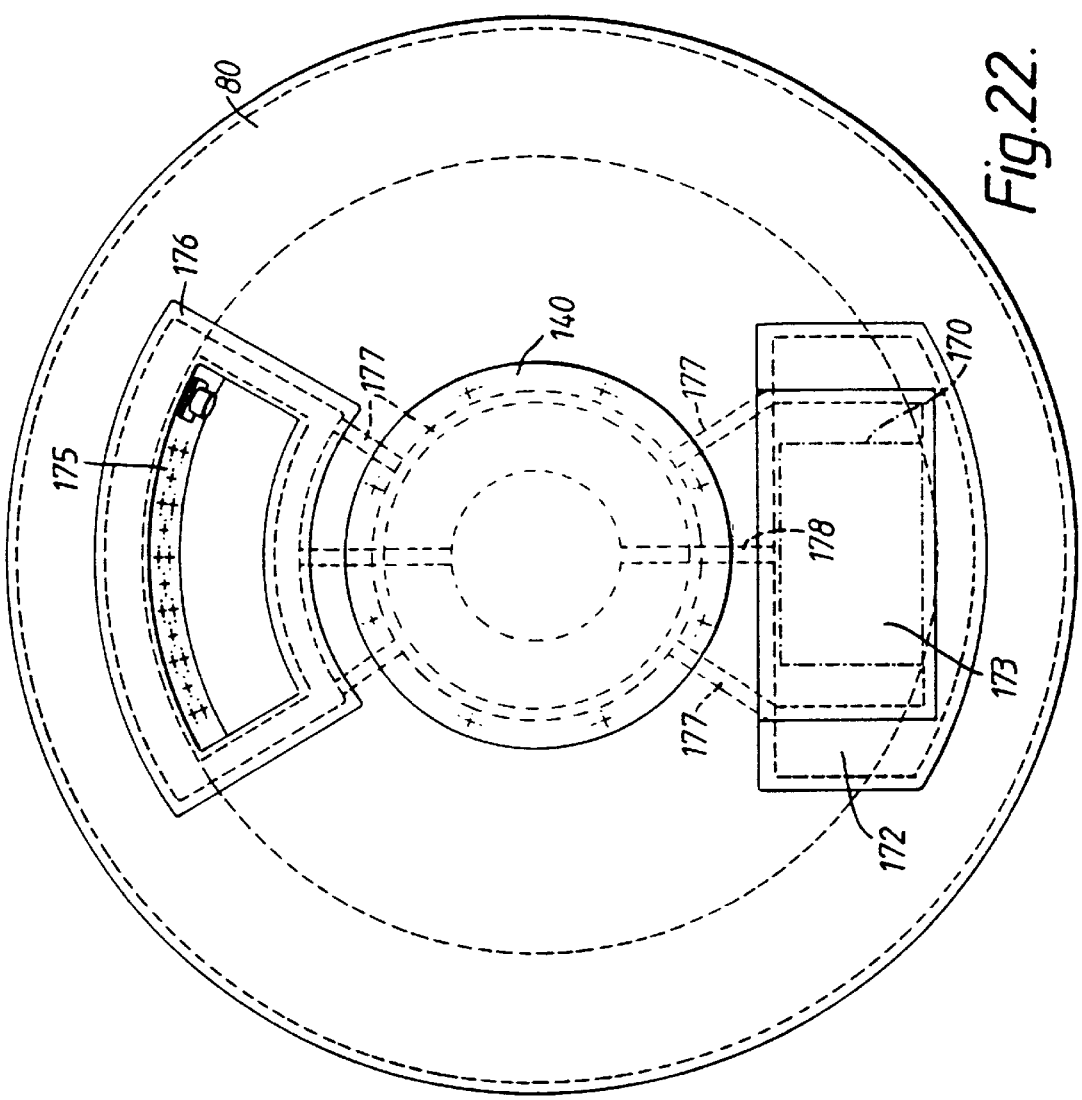
FIG. 22 shows a top plan view of the modification of FIG. 21.
Figure 21:
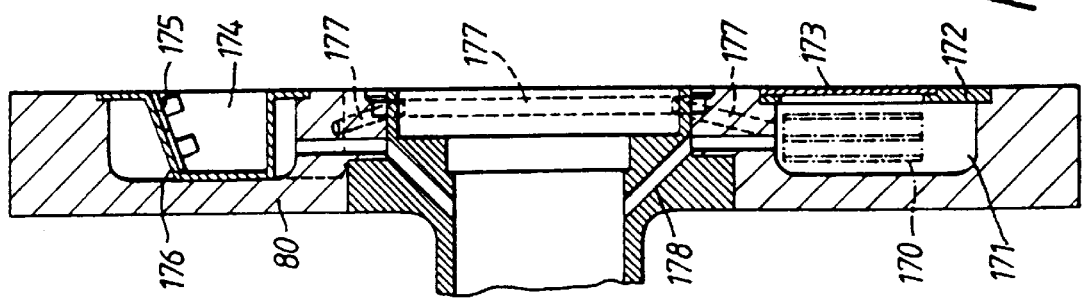
FIG. 21 shows an axial section through a modification of any one of the centrifuge versions of FIGS. 1 to 13 and 18 to 20.

A problem sometimes encountered with transmission of analogue data signals from instrumentation at the rotating sample(s) is that electrical interference, produced by controllers for the drive motors (such as 136 and 141) and/or by the slip rings (such as 143) and/or extraneously distorts the analogue signals, with the result that incorrect or unintelligible readings are obtained. In order to mitigate this problem, the modification shown in FIGS. 21 and 22 may be made. The diametral plate 80 carries a computer 170 within a recess 171 closed by a main lid 172 and an auxiliary lid 173. A recess 174 diametrically opposite to the recess 171 contains a dish 176 supporting electrical terminals 175 connected by electrical leads (not shown) to detection and measurement instrumentation associated with the sample(s). Other electrical leads (not shown) extend from the terminals 175 to the computer 170 through ducts 177 formed in the interior of the plate 80. The computer 170 converts the analogue signals received from the instrumentation into digital signals which are transmitted, via further electrical leads (not shown) extending through ducts 178, to slip rings corresponding to the slip rings 143 but much less in number. In this way, the deleterious effects of electrical interference upon the readings obtained can be mitigated and the number of slip rings (143) and their associated electrical leads can be very significantly reduced.

Figure 23:
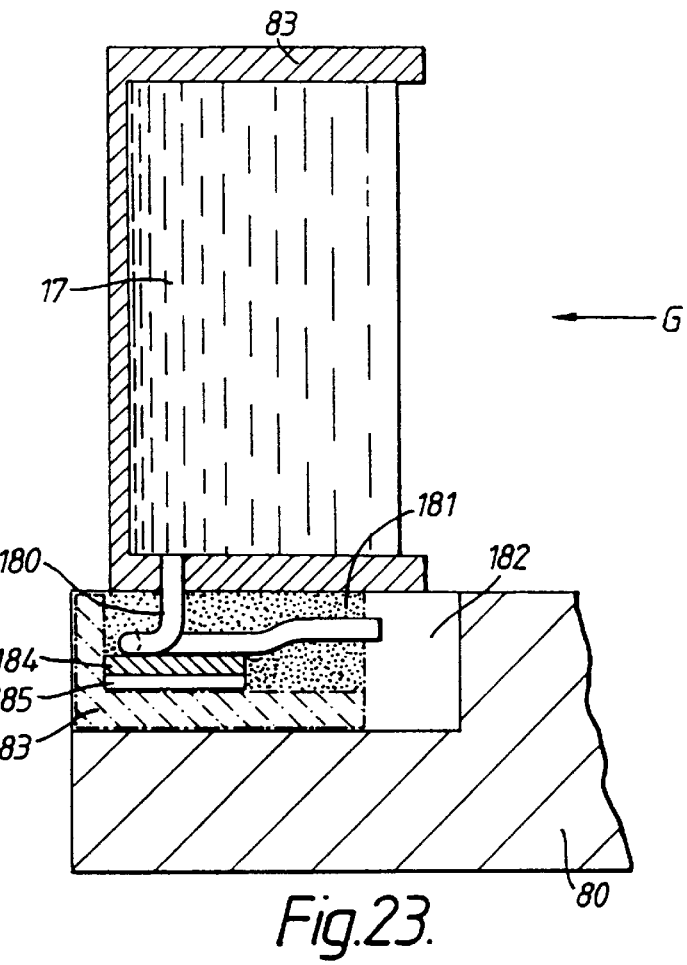
FIG. 23 shows a fragmentary axial section through another modification of any one of the centrifuge versions of FIGS. 1 to 13 and 18 to 20.
Figure 24:
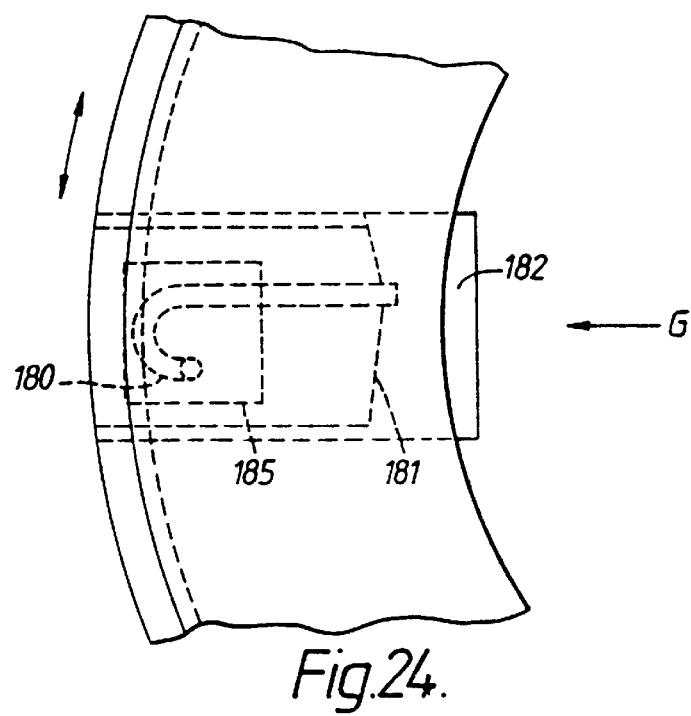
FIG. 24 shows a fragmentary top plan view of the modification of FIG. 23.
Figure 25:
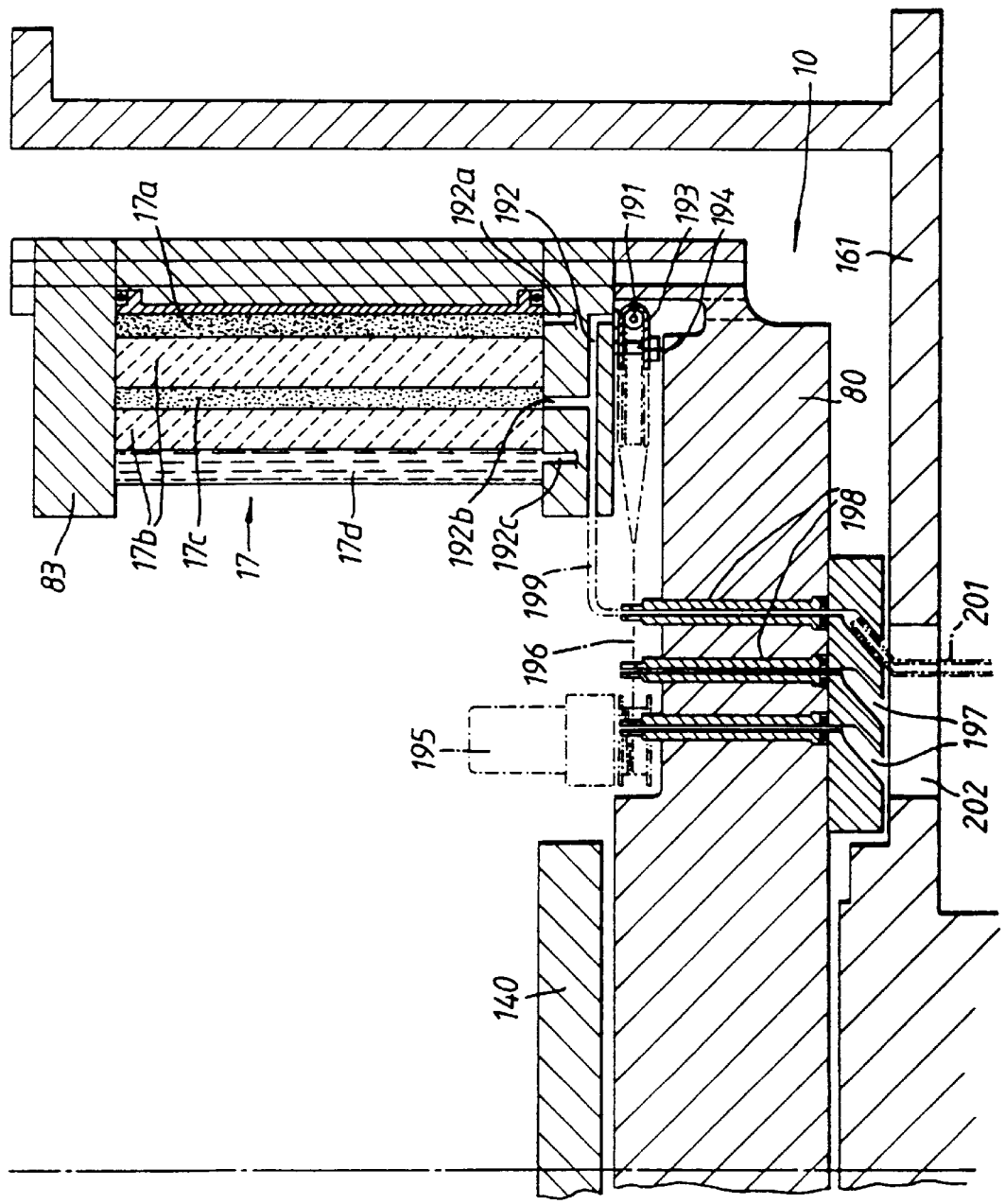
FIG. 25 shows a fragmentary half-section through a further modification of any one of the centrifuge versions of FIGS. 1 to 13 and 18 to 20.

It is frequently desired to control the flow of liquid, particularly water, from the sample(s) 17, especially a sample 17 such as shown in FIG. 25, under the high g forces, but conventional valves are unreliable since the high forces upon their moving parts can cause them to alfunction. This problem can be overcome by employing the modification of FIGS. 23 and 24. Duct means in the form of a metal tube 180 extends from adjacent the outer periphery of the sample 17 to a location in the plate 18 radially inwards of that outer periphery, the radial extent of the tube 180 being set to determine the radial water level in the sample 17 during high-speed rotation. The tube 180 extends in thermal insulation 181 in a recess 182 in the plate 80, the recess 182 also containing a good thermally conductive support 183. Bonded to the tube 180 in a good thermally conductive manner is a plate 184 of good thermal conductivity, between which and the support 183 is fitted a Peltier-effect device 185.

The passing of electric current through the device 185 produces a steep temperature gradient between the support 183 and the plate 184. If the plate 184 constitutes the "cold"=0 side of the device 185, then any water in the tube 180 can be frozen to obstruct water flow through the tube.

By careful control of the current supply to the device 185, thereby carefully to control the temperature of the plate 184, the permitted water flow through the tube 180 can be reduced and increased as desired.

In the modification shown in FIG. 25, there is again seen the container or drum 10 consisting of the plate 80 and the ring channel 83, which is releasably attached by bolts (of which one is seen and referenced 190) to the plate 80. The scale model sample 17 here consists of an outer layer 17a of sand, two clay layers 17b sandwiching a sand acquifer layer 17c between them and an inner layer 17d of water. A system of maintaining constant pressure in the water in the aquifer layer 17c and allowing flow of the water into or out of the aquifer layer 17c at that constant pressure is illustrated; it includes duct means in the form of a flexible tube 191 connected to the outlet of a bore 192 through the lowest wall of the ring channel 83. By way of branch bores 192a, 192b and 192c communicable with various locations spaced radially of the interior of the channel 83 (the bore 192b being shown open and the bores 192a and 192c shown closed), the bore 192 communicates with a selected region of hydraulic pressure in the interior of the channel 83 during centrifuging. The bore 192 is connected to a pipe 199 which is constantly supplied with a flow of water and the bore is maintained at a selected pressure by continual overflow of water from the adjustable outlet provided by the outlet end of the pipe 191. The system includes a horizontal channel piece 193 mounted upon a vertical pivot 194 and turnable thereon against the action of centrifugal force by a motorized winch 195 connected to the channel piece 193 by a cable 196. The position of the outlet end of the tube 191 radially of the drum during centrifuging determines the hydraulic head in the sample 17 and that position is adjustable by means of the winch 195 during centrifuging. In order simply and yet efficaciously to introduce water into one or more pipes such as the pipe 199, the plate 80 is provided co-axially with one or more, in this case three, annular recesses 197 at its underside. These recesses 197 open towards the axis of the centrifuge and are connected to a corresponding number of sets of connecting tubes 198 of which the tubes in each set are distributed in an arc about the axis of the centrifuge. These tubes 198 are themselves connected to the respective pipes (of which the pipe 199 is shown) themselves connected to the right-angled bores 192a to 192c in the ring channel. Each such bore is fitted with a sealing plug and when this is removed a connection is established between the water in the pipe 199 and the water in the sample 17 near to the end of the open bore. Water is injected into the recesses 197 by one or more stationary supply conduits or nozzles 201 extending through a hole or holes 202 in the base wall of the casing 161. As the plate 80 rotates, centrifugal force causes the water to flow from the recesses 197 through duct means constituted by the tubes 198 and the pipes 199, past the open bores 192b, and on to the outlet end of the tube 191 where it continually overflows. This controls the pressure of water at the end of the open bores 192b, and allows water either to drain into or out of the bores 192b as may be demanded by the sample 17 at any particular stage of an experiment. If desired, there can be a plurality of nozzles 201 supplying liquid at differing rates of flow or differing liquids to a plurality of recesses 197.

The invention is applicable to increasing the maximum centrifugal force obtainable with centrifuges, to increasing the versatility of centrifuges and to improving the design of structures on dry land and on the seabed, inter alia.

I claim:

1. A geotechnical centrifuge comprising a rotary element having an axis, outer peripheral portions of said element concentric with said axis, said element being rotatable about said axis, rotary receiving means releasably attached to said element at the face of said element in the region of said peripheral portions, for containing a geotechnical scale modelling sample, and means for rotating said element about said axis at a speed sufficient to centrifuge a geotechnical sample that is contained in said rotary receiving means.

2. A centrifuge according to claim 1, wherein said element and said receiving means constitute a drum.

3. A centrifuge according to claim 1, wherein said element is massive relative to said receiving means.

4. A geotechnical centrifuge comprising stationary means, a member rotatable about an axis relative to said stationary means, geotechnical scale modelling sample carried by said member at a spacing from said axis, tilting means arranged to tilt said member relative to said stationary means so as to tilt said axis between a substantially vertical first condition and a second condition at a substantial angle to the vertical, and means for rotating said member around said axis for centrifuging said sample.

5. A centrifuge according to claim 4, wherein said member comprises a substantially horizontal rotary element having an axis, and outer peripheral portions of said element concentric with said axis, said element being rotatable about said axis, and said centrifuge further comprises rotary receiving means supported by said element and located in the region of said outer peripheral portions.

6. A centrifuge according to claim 5, wherein said element and said receiving means constitute a drum.

7. A centrifuge according to claim 5, wherein said element is massive relative to said receiving means.

8. A centrifuge comprising a member rotatable about an axis, a model carried by said member at a spacing from said axis, and tilting means arranged to tilt said member so as to tilt said axis between a substantially vertical first condition and a second condition at a substantial angle to the vertical, wherein said member comprises a substantially horizontal rotary wall having an axis, and an annular outer periphery of said wall concentric with said axis, said wall being rotatable about said axis, and said centrifuge further comprises rotary receiving means supported by said wall and located in the region of said outer periphery.

9. A centrifuge according to claim 8, wherein said member is a drum.

10. A centrifuge according to claim 4, wherein said second condition is substantially horizontal.

11. A geotechnical centrifuging method comprising rotating, relative to stationary means, a geotechnical centrifuge member and a geotechnical scale modelling sample carried thereby while the axis of rotation of the centrifuge member is at a substantial angle to the vertical, and then tilting said member and said sample relative to said stationary means to tilt said axis to a substantially vertical condition while said centrifuge member and said sample continue to rotate about said axis, and continuing to rotate said centrifuge member and said sample about said axis in the latter condition.

12. A method according to claim 11, wherein said substantial angle is substantially a right-angle.

13. A method of centrifuging a geotechnical sample comprising:
providing a geotechnical sample,
providing a member that is rotatable about an axis of rotation for centrifuging said geotechnical sample, positioning said geotechnical sample on said member in spaced relation to said axis when said axis is in a first orientation, tilting said axis to a second orientation after said sample has been positioned on said member, and rotating said member about said second orientation to centrifuge said sample.

14. A method of centrifuging a geotechnical sample as defined in claim 13, in which said steps of providing a member and of providing a sample comprise providing said member with a mass that is much larger than the mass of said geotechnical sample.

* * * * *